(12) United States Patent
Dinca et al.

(10) Patent No.: US 10,174,063 B2
(45) Date of Patent: Jan. 8, 2019

(54) COMPOSITIONS AND METHODS COMPRISING CONDUCTIVE METAL ORGANIC FRAMEWORKS AND USES THEREOF

(71) Applicant: Massachusetts Institute of Technology, Cambridge, MA (US)

(72) Inventors: Mircea Dinca, Belmont, MA (US); Dennis Sheberla, Watertown, MA (US); Lei Sun, Cambridge, MA (US); Casey R. Wade, Waltham, MA (US); Michael Glenn Campbell, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/309,023

(22) PCT Filed: May 6, 2015

(86) PCT No.: PCT/US2015/029503
§ 371 (c)(1),
(2) Date: Nov. 4, 2016

(87) PCT Pub. No.: WO2015/171791
PCT Pub. Date: Nov. 12, 2015

(65) Prior Publication Data
US 2017/0073364 A1    Mar. 16, 2017

Related U.S. Application Data

(60) Provisional application No. 62/091,100, filed on Dec. 12, 2014, provisional application No. 61/988,952, filed on May 6, 2014.

(51) Int. Cl.
| | | |
|---|---|---|
| *C07F 15/04* | (2006.01) | |
| *B01J 20/22* | (2006.01) | |
| *C07F 15/06* | (2006.01) | |
| *C07F 1/00* | (2006.01) | |
| *C07F 1/08* | (2006.01) | |
| *H01G 11/30* | (2013.01) | |

(52) U.S. Cl.
CPC ........... *C07F 15/045* (2013.01); *B01J 20/226* (2013.01); *C07F 1/005* (2013.01); *C07F 1/08* (2013.01); *C07F 15/065* (2013.01); *H01G 11/30* (2013.01)

(58) Field of Classification Search
CPC .......... C07F 15/045; C07F 1/005; C07F 1/08; C07F 15/065
See application file for complete search history.

(56) References Cited

U.S. PATENT DOCUMENTS

| | | | |
|---|---|---|---|
| 5,112,974 A * | 5/1992 | Barton | C07D 471/04 204/157.72 |
| 6,893,564 B2 | 5/2005 | Mueller et al. | |
| 7,215,473 B2 | 5/2007 | Fleming | |
| 7,662,746 B2 | 2/2010 | Yaghi et al. | |
| 8,197,579 B2 | 6/2012 | Miller | |
| 8,372,779 B2 | 2/2013 | Schubert et al. | |
| 8,764,887 B2 | 7/2014 | Dinca et al. | |
| 9,758,532 B2 * | 9/2017 | Dinca | C07F 3/06 |
| 2001/0003950 A1 | 6/2001 | Zhang et al. | |
| 2007/0171107 A1 | 7/2007 | Wang | |
| 2008/0188677 A1 | 8/2008 | Schubert et al. | |
| 2008/0306315 A1 | 12/2008 | Lillerud et al. | |
| 2009/0221418 A1 | 9/2009 | Fischer et al. | |
| 2010/0197990 A1 | 8/2010 | Schubert et al. | |
| 2010/0322837 A1 | 12/2010 | Miller | |
| 2011/0137100 A1 | 6/2011 | Toulhoat et al. | |
| 2011/0294658 A1 | 12/2011 | Lefevre et al. | |
| 2012/0077667 A1 | 3/2012 | Liu et al. | |
| 2012/0141685 A1 | 6/2012 | Gaab et al. | |
| 2013/0066128 A1 | 3/2013 | Breuil et al. | |
| 2013/0152789 A1 | 6/2013 | Polshettiwar et al. | |
| 2013/0204025 A1 | 8/2013 | Buso et al. | |
| 2014/0012039 A1 | 1/2014 | Yaghi et al. | |
| 2014/0326007 A1 | 11/2014 | Dinca et al. | |
| 2015/0047505 A1 | 2/2015 | Schroder et al. | |
| 2016/0102040 A1 | 4/2016 | Allen et al. | |
| 2017/0341010 A1 | 11/2017 | Dinca et al. | |

FOREIGN PATENT DOCUMENTS

| | | |
|---|---|---|
| CN | 104001476 B | 5/2016 |
| WO | WO 2014/182648 A1 | 11/2014 |
| WO | WO 2015/142954 A1 | 9/2015 |
| WO | WO 2015/171791 A1 | 11/2015 |
| WO | WO 2017/048787 A1 | 3/2017 |
| WO | WO 2017/048795 A1 | 3/2017 |
| WO | WO 2018/067636 A1 | 4/2018 |

OTHER PUBLICATIONS

International Search Report and Written Opinion for PCT/US2015/029503 dated Aug. 21, 2015.
International Preliminary Report on Patentability for PCT/US2015/029503 dated Nov. 17, 2016.
Noro et al., Metal-organic thin-film transistor (MOTFT) based on a bis(o-diiminobenzosemiquinonate) nickel(II) complex. J Am Chem Soc. Jul. 20, 2005;127(28):10012-3.
Sheberla et al., High electrical conductivity in $Ni_3(2,3,6,7,10,11$-hexaiminotriphenylene$)_2$, a semiconducting metal-organic graphene analogue. J Am Chem Soc. Jun. 25, 2014;136(25):8859-62. doi: 10.1021/ja502765n.
Dinca, Teaching Sponges New Tricks: Small Molecule Chemistry and Charge Transport in Microporous Metal-Organic Frameworks. NSF Center for Chemical Innovation. Brown University. Providence, RI. May 2014. 4 pages.

(Continued)

*Primary Examiner* — Pancham Bakshi
(74) *Attorney, Agent, or Firm* — Wolf, Greenfield & Sacks, P.C.

(57) ABSTRACT

Compositions and methods comprising metal organic frameworks (MOFs) and related uses are generally provided. In some embodiments, a MOF comprises a plurality of metal ions, each coordinated with at least one ligand comprising at least two sets of ortho-diimine groups arranged about an organic core.

26 Claims, 14 Drawing Sheets

(56) References Cited

OTHER PUBLICATIONS

Herebian et al., Molecular and electronic structures of bis-(o-diiminobenzosemiquinonato)metal(II) complexes (Ni, Pd, Pt), their monocations and -anions, and of dimeric dications containing weak metal-metal bonds. J Am Chem Soc. Jul. 30, 2003;125(30):9116-28.
Abbenhuis, Heterogenization of Metallocene Catalysts for Alkene Polymerization. Angew. Chem. Int. Ed. 1999;38(8):1058-60.
Akiyama et al., Effect of functional groups in MIL-101 on water sorption behavior. Microporous and Mesoporous Materials. 2012;157:89-93.
Alarco-Padilla et al., Application of absorption heat pumps to multi-effect distillation: a case study of solar desalination. Desalination. Jun. 25, 2007;212:294-302.
Al-Sa'Doun, Dimerization of ethylene to butene-1 catalyzed by Ti(OR')4-AlR3. Applied Catalysis A. Nov. 2, 1993;105(1):1-40.
Askalany et al., An overview on adsorption pairs for cooling. Renewable and Sustainable Energy Reviews. Mar. 2013;19:565-72.
Baier et al., Post-Metallocenes in the Industrial Production of Polyolefins. Ange. Chemie Int. Ed. Sep. 8, 2014;53(37):9722-44.
Bellarosa et al. When the Solvent Locks the Cage: Theoretical Insight into the Transmetalation of MOF-5 Lattices and Its Kinetic Limitations. Chem. Mater. 2015;27(9):3422-9. Epub Apr. 13, 2015.
Biswas et al., A cubic coordination framework constructed from benzobistriazolate ligands and zinc ions having selective gas sorption properties. Dalton Trans. 2009:6487-95. Epub Jun. 29, 2009.
Biswas et al., Homo- and Heteropentanuclear Coordination Compounds with Td Symmetry—the Solid State Structures of [MZn4(L)4(L')6] (M=CoII or Zn; L=chloride or acac; L'=1,2,3-benzotriazolate). Z. Anorg. Allg. Chem. Oct. 2008;634(14):2532-8.
Biswas et al., Syntheses and Magnetostructural Investigations on Kuratowski-Type Homo- and Heteropentanuclear Coordination Compounds [MZn4Cl4(L)6] (MII=Zn, Fe, Co, Ni, or Cu; L=5,6-Dimethyl-1,2,3-benzotriazolate) Represented by the Nonplanar K3,3 Graph. Inorg. Chem. 2010;49(16):7424-34. Epub Jul. 16, 2010.
Bonaccorsi et al., Hydrothermal and microwave synthesis of SAPO (CHA) zeolites on aluminum foams for heat pumping applications. Microporous and Mesoporous Mater. 2013;167:30-37.
Boudjouk et al., Solvated and Unsolvated Anhydrous Metal Chlorides from Metal Chloride Hydrates. Inorg. Synth. 1992;29:108-11.
Brozek et al., Cation exchange at the secondary building units of metal-organic frameworks. Chem. Soc. Rev. 2014;43:5456-67. Epub May 16, 2014.
Brozek et al., Dynamic DMF Binding in MOF-5 Enables the Formation of Metastable Cobalt-Substituted MOF-5 Analogues. ACS Cent. Sci. 2015;1(5):252-60. Epub Jul. 29, 2015.
Brozek et al., Lattice-imposed geometry in metal-organic frameworks: lacunary Zn4O clusters in MOF-5 serve as tripodal chelating ligands for Ni2+. Chemical Science. 2012;3:2110-3. Epub Apr. 4, 2012.
Brozek et al., No Disproportionation at a Mononuclear Site-Isolated Fe2+ Center in Fe2+-MOF-5. J. Am. Chem. Soc. 2015;137(23):7495-501. Epub May 19, 2015.
Brozek et al., Solvent-Dependent Cation Exchange in Metal-Organic Frameworks. Chem. Eur. J. Jun. 2, 2014;20(23):6871-4.
Brozek et al., Ti3+-, V2+/3+-, Cr2+/3+-, Mn2+-, and Fe2+-Substituted MOF-5 and Redox Reactivity in Cr- and Fe-MOF-5. J. Am. Chem. Soc. 2013;135(34):12886-91. Epub Jul. 31, 2013.
Cadiau et al., Design of Hydrophilic Metal Organic Framework Water Adsorbents for Heat Reallocation. Adv. Mater. 2015;27:4775-80. Epub Aug. 26, 2015.
Campbell et al., Chemiresistive Sensor Arrays from Conductive 2D Metal-Organic Frameworks. J. Am. Chem. Soc. 2015;137(43):13780-3. Epub Oct. 11, 2015.
Canivet et al., MOF-Supported Selective Ethylene Dimerization Single-Site Catalysts through One-Pot Postsynthetic Modification. J. Am. Chem. Soc. 2013;135:4195-8. Epub Mar. 7, 2013.
Canivet et al., Structure—property relationships of water adsorption in metal-organic frameworks. New J. Chem. 2014;38:3102-11. Epub Apr. 16, 2014.

Canivet et al., Water adsorption in MOFs: fundamentals and applications. Chem. Soc. Rev. 2014;43:5594-617. Epub May 29, 2014.
Caskey et al., Dramatic tuning of carbon dioxide uptake via metal substitution in a coordination polymer with cylindrical pores. J Am Chem Soc. Aug. 20, 2008;130(33):10870-1. doi: 10.1021/ja8036096. Epub Jul. 29, 2008.
Chmiola et al., Anomalous Increase in Carbon Capacitance at Pore Sizes Less Than 1 Nanometer. Science. Sep. 22, 2006;313(5794):1760-3.
Chmiola et al., Desolvation of Ions in Subnanometer Pores and Its Effect on Capacitance and Double-Layer Theory. Angew. Chem. Int. Ed. Apr. 21, 2008;47(18):3392-5.
Choi et al., Broadly hysteretic H2 adsorption in the microporous metal-organic framework Co(1,4-benzenedipyrazolate). J Am Chem Soc. Jun. 25, 2008;130(25):7848-50. doi: 10.1021/ja8024092. Epub May 31, 2008.
Choi et al., Hydrogen storage in water-stable metal-organic frameworks incorporating 1,3- and 1,4-benzenedipyrazolate. Energy Environ. Sci. 2010;3:117-23. Epub Nov. 4, 2009.
Choi et al., Supported Single-Site Catalysts for Slurry and Gas-Phase Olefin Polymerisation. Can. J. of Chem. Eng. Jun. 2012;90:646-71.
Church et al., A New Multicomponent Reaction Catalyzed by a [Lewis Acid]+[Co(CO)4]-Catalyst: Stereospecific Synthesis of 1,3-Oxazinane-2,4-diones from Epoxides, Isocyanates, and CO. J. Am. Chem. Soc. 2007;129(26):8156-62. Epub Jun. 12, 2007. Abstract Only.
Church et al., Carbonylation of heterocycles by homogeneous catalysts. Chem. Commun. 2007;7:657-74. Epub Jan. 19, 2007.
Coasne et al., Temperature Effect on Adsorption/Desorption Isotherms for a Simple Fluid Confined within Various Nanopores. Adsorption. Jul. 2005;11:289-94.
Colombo et al., High thermal and chemical stability in pyrazolate-bridged metal-organic frameworks with exposed metal sites. Chem. Sci. 2011;2:1311-9. Epub Apr. 28, 2011.
Comito et al., Single-Site Heterogeneous Catalysts for Olefin Polymerization Enabled by Cation Exchange in a Metal-Organic Framework. J. Am. Chem. Soc. 2016;138(32):10232-7. Epub Jul. 21, 2016. Supporting Information Included.
Corma et al., Engineering Metal Organic Frameworks for Heterogeneous Catalysis. Chem. Rev. 2010;110(8):4606-55. Epub Apr. 1, 2010.
Critoph, Evaluation of alternative refrigerant—adsorbent pairs for refrigeration cycles. Applied Thermal Engineering. Nov. 1996;16(11):891-900.
Cychosz et al., Water stability of microporous coordination polymers and the adsorption of pharmaceuticals from water. Langmuir. Nov. 16, 2010;26(22):17198-202. doi: 10.1021/la103234u. Epub Oct. 5, 2010.
De Lange et al., Adsorption-Driven Heat Pumps: The Potential of Metal-Organic Frameworks. Chem. Rev. 2015;115(22):12205-50. Epub Oct. 23, 2015.
De Lange et al., Metal-Organic Frameworks in Adsorption-Driven Heat Pumps: The Potential of Alcohols as Working Fluids. Langmuir. 2015;31(46):12783-96. Epub Nov. 2, 2015.
Denysenko et al., Elucidating Gating Effects for Hydrogen Sorption in MFU-4-Type Triazolate-Based Metal-Organic Frameworks Featuring Different Pore Sizes. Chem. Eur. J. 2011;17(6):1837-48. Epub Jan. 12, 2011.
Denysenko et al., Postsynthetic Metal and Ligand Exchange in MFUA-41: A Screening Approach toward Functional Metal-Organic Frameworks Comprising Single-Site Active Centers. Chem. Eur. J. May 26, 2015;21(22):8188-99.
Denysenko et al., Reversible gas-phase redox processes catalyzed by Co-exchanged MFU-41(arge). Chem. Commun. 2012;48:1236-8. Epub Dec. 6, 2011.
Denysenko et al., Scorpionate-Type Coordination in MFU-41 Metal-Organic Frameworks: Small-Molecule Binding and Activation upon the Thermally Activated Formation of Open Metal Sites. Angew. Chemie Int. Ed. Jun. 2, 2014;53(23):5832-6.
Deria et al., Beyond post-synthesis modification: evolution of metal-organic frameworks via building block replacement. Chem. Soc. Rev. 2014;43:5896-912. Epub Apr. 11, 2014.

(56) References Cited

OTHER PUBLICATIONS

Desantis et al., Techno-economic Analysis of Metal-Organic Frameworks for Hydrogen and Natural Gas Storage. Energy Fuels. 2017;31(2):2024-32. Epub Jan. 4, 2017.
Dinca et al., Dalton Lecture: New Application of Metal-Organic Frameworks. UC Berkeley. Mar. 11, 2016. 49 pages.
Dinca et al., Designer Porous material for Clean Energy and Water. International Workshop on Advanced Materials. Al Hamra Fort, Ras al Khaimah, UAE. Feb. 2017 7 pages.
Dinca et al., Teaching Sponges New Tricks: Redox Reactivity and Charge Transport in Microporous Metal-Organic Frameworks. Princeton University. Frick Chemistry Laboratory, Taylor Auditorium. Princeton, NJ. Sep. 14, 2015. 48 pages.
Dinca, Dynamic MOF SBUs as Active Sites for Small Molecule Reactivity and Catalysis. 253rd National ACS Meeting. San Francisco, CA. Apr. 2017 10 pages.
Domski et al., Living alkene polymerization: New methods for the precision synthesis of polyolefins. Progress in Polymer Science. Jan. 2007;32(1):30-92.
Doonan et al., Exceptional ammonia uptake by a covalent organic framework. Nature Chemistry. 2010;2:235-8. Epub Feb. 7, 2010.
Ehrenmann et al., Water adsorption characteristics on MIL-101 for heat-transformation application of MOFs. Eur J Inorg Chem. 2011;2011(4):471-474.
Farrusseng et al., Metal-Organic Frameworks: Opportunities for Catalysis. Angew. Chemie Int. Ed. Sep. 28, 2009;48(41):7502-13.
Feigl et al., Über Verbindungen des Nickels mito-Phenylendiamin und 1, 3, 4-Toluylendiamin. Monatsh. Chem. Jul. 1927;48(7):445-50. Only structures were considered as no translation was provided.
Férey et al., A Chromium Terephthalate-Based Solid with Unusually Large Pore Volumes and Surface Area. Science. Sep. 23, 2005;309(5743):2040-2.
Finiels et al., Nickel-based solid catalysts for ethylene oligomerization—a review. Catal. Sci. Technol. 2014;4:2412-26. Epub Apr. 16, 2014.
Froehlich et al., Multicycle water vapour stability of microporous breathing MOF aluminium isophthalate CAU-10-H. Dalton Trans. 2014;43:15300-4. Epub Aug. 26, 2014.
Furlan et al., Highly active zirconium(IV) catalyst containing sterically hindered hydridotris(pyrazolyl)borate ligand for the polymerization of ethylene. Macromolecular Rapid Communications. Oct. 2000;21(15):1054-7.
Furukawa et al., Water adsorption in porous metal-organic frameworks and related materials. J Am Chem Soc. Mar. 19, 2014;136(11):4369-81. doi: 10.1021/ja500330a. Epub Mar. 11, 2014.
Garcia-Orozco et al., Tris(pyrazolyl)methane-chromium(III) complexes as highly active catalysts for ethylene polymerization. Journal of Molecular Catalysis A: Chemical. Dec. 2006;260(1-2):70-6.
Gargiulo et al., Synthesis and characterization of a microporous copper triazolate as a water vapor adsorbent. Microporous and Mesoporous Mater. 2011;145:74-9.
Garzón-Tovar et al., Optimised room temperature, water-based synthesis of CPO-27-M metal-organic frameworks with high space-time yields. J. Mater. Chem. A. 2015;3:20819-26. Epub Sep. 9, 2015.
Getzler et al., Synthesis of β-Lactones: A Highly Active and Selective Catalyst for Epoxide Carbonylation. J. Am. Chem. Soc. 2002;124(7):1174-5. Epub Jan. 24, 2002.
Gil et al., Copolymerization of Ethylene with 1-Hexene Using Sterically Hindered Tris(pyrazolyl)borate Titanium (IV) Compounds. Macromolecular Chemistry and Physics. Jan. 2001;202(2):319-24.
Golubovic et al., Sorption properties for different types of molecular sieve and their influence on optimum dehumidification performance of desiccant wheels. Int. J. Heat Mass Transf. Aug. 2006;49(17-18):2802-9.
Guo et al., Adsorption of NH3 onto activated carbon prepared from palm shells impregnated with H2SO4. Journal of Colloid and Interface Science. Jan. 15, 2005;281(2):285-90.

Henninger et al., Characterisation and improvement of sorption materials with molecular modeling for the use of heat transformation applications. Adsorption. 2011;17:833-43.
Henninger et al., MOFs as adsorbents for low temperature heating and cooling applications. J Am Chem Soc. Mar. 4, 2009;131(8):2776-7. doi: 10.1021/ja808444z.
Henninger et al., MOFs for Use in Adsorption Heat Pump Processes. European Journal of Inorganic Chemistry. Jun. 2012; 2012(16): 2625-34.
Henninger et al., Novel sorption materials for solar heating and cooling. Energy Procedia. 2012;30:279-88.
Henninger et al., Water adsorption characteristics of novel materials for heat transformation applications. Appl. Therm. Eng. 2010;30:1692-1702.
Hermes et al., Selective Nucleation and Growth of Metal-Organic Open Framework Thin Films on Patterned COOH/CF3-Terminated Self-Assembled Monolayers on Au(111). JACS. 2005;127:13744-5.
Hlatky, Heterogeneous Single-Site Catalysts for Olefin Polymerization. Chem. Rev. 2000;100:1347-76.
House et al., The synthesis and X-ray structure of trans-[CrCl2(nPrNH2)4]BF4•H2O and the thermal and Hg2+-assisted chloride release kinetics from some trans-[CrCl2(N)4]+ complexes. Inorganica Chimica Acta. Sep. 1995;237(1-2):37-46.
Janchen et al., Studies of the water adsorption on Zeolites and modified mesoporous materials for seasonal storage of solar heat. Solar Energy. 2004;76:339-44.
Jasuja et al., Adjusting the Stability of Metal-Organic Frameworks under Humid Conditions by Ligand Functionalization. Langmuir. 2012;28(49):16874-80. Epub Nov. 7, 2012.
Jeon et al., Accelerated Life-time Tests including Different Load Cycling Protocols for High Temperature Polymer Electrolyte Membrane Fuel Cells. Electrochimica Acta. Dec. 1, 2014;148:15-25.
Jeremias et al., MIL-100(Al, Fe) as water adsorbents for heat transformation purposes—a promising application. J Mater Chem. 2012;22:10148-10151.
Jeremias et al., Programming MOFs for water sorption: amino-functionalized MIL-125 and UiO-66 for heat transformation and heat storage applications. Dalton Trans. Dec. 7, 2013;42(45):15967-73. doi: 10.1039/c3dt51471d. Epub Jul. 18, 2013.
Jeremias et al., Water and methanol adsorption on MOFs for cycling heat transformation processes. New J Chem. 2014;38:1846-52.
Kaminsky et al., High melting polypropenes by silica-supported zirconocene catalysts. Makromol. Chem. Rapid. Commun. 1993;14:239-43.
Katz et al., High volumetric uptake of ammonia using Cu-MOF-74/Cu-CPO-27 . Dalton Trans. 2016;45:4150-3. Epub Sep. 24, 2015.
Khutia et al., Water sorption cycle measurements on functionalized MIL-101 Cr for heat transformation application. Chem Mater. 2013;25:790-798.
Killian et al., Preparation of Linear α-Olefins Using Cationic Nickel(II) α-Diimine Catalysts. Organometallics. 1997;16(10):2005-7. Epub May 13, 1997.
Klet et al., Single-Site Organozirconium Catalyst Embedded in a Metal-Organic Framework. J. Am. Chem. Soc. 2015;137(50):15680-83. Epub Dec. 14, 2015.
Kramer et al., Practical β-Lactone Synthesis: Epoxide Carbonylation at 1 atm. Org. Lett. 2006;8(17):3709-12. Epub Jul. 18, 2006.
Kunrath et al., Highly Selective Nickel Ethylene Oligomerization Catalysts Based on Sterically Hindered Tris(pyrazolyl)borate Ligands. Organometallics. 2003;22:4739-43. Epub Oct. 9, 2003.
Kusgens et al., Characterization of metal-organic frameworks by water adsorption. Microporous and Mesoporous Mater. 2009;120:325-330.
Lallemand et al., Catalytic oligomerization of ethylene over Ni-containing dealuminated Y zeolites. Appl. Catal. A Gen. Feb. 2006;301:196-201.
Lallemand et al., Ethylene oligomerization over Ni-containing mesostructured catalysts with MCM-41, MCM-48 and SBA-15 topologies. Studies in Surface Science and Catalysis. 2007;170:1863-9. Epub Oct. 18, 2007.

(56) References Cited

OTHER PUBLICATIONS

Lallemand et al., Ni-MCM-36 and Ni-MCM-22 catalysts for the ethylene oligomerization. Studies in Surface Science and Catalysis. 2008;174:1139-42. Epub Nov. 6, 2008.
Li et al., Design and synthesis of an exceptionally stable and highly porous metal-organic framework. Nature. 1999;402:276-9. Epub Nov. 18, 1999.
Li et al., Highly active self-immobilized FI-Zr catalysts in a PCP framework for ethylene polymerization. Chem. Commun. 2015;51:16703-6. Epub Sep. 21, 2015.
Li et al., Reductive electrosynthesis of Crystalline Metal-Organic frameworks. JACS. 2011;133:12926-9.
Liao et al., Drastic Enhancement of Catalytic Activity via Post-oxidation of a Porous MnII Triazolate Framework. Chem. Eur. J. Sep. 1, 2014;20(36):11303-7.
Liu et al., High-Performance Chemical Sensing Using Schottky-Contacted Chemical Vapor Deposition Grown Monolayer MoS2 Transistors. ACS Nano. 2014;8(5):5304-14. Epub Apr. 21, 2014.
Liu et al., Postsynthetic modification of mixed-linker metal-organic frameworks for ethylene oligomerization. RSC Adv. 2014;4:62343-6. Epub Nov. 13, 2014.
Liu et al., Single-Walled Carbon Nanotube-Metalloporphyrin Chemiresistive Gas Sensor Arrays for Volatile Organic Compounds. Chem. Mater. 2015;27(10):3560-3. Epub May 8, 2015.
Low et al., Virtual high throughput screening confirmed experimentally: porous coordination polymer hydration. J. Am. Chem. Soc. Nov. 4, 2009;131(43):15834-42. doi: 10.1021/ja9061344.
Luna et al., Evaluation of Commercial Off-the-Shelf Sorbents and Catalysts for Control of Ammonia and Carbon Monoxide. American Institute of Aeronautics and Astronautics. 2008. 15 pages.
Ma et al., A series of isoreticular chiral metal-organic frameworks as a tunable platform for asymmetric catalysis. Nat. Chem. 2010;2:838-46. Epub Jul. 25, 2010.
Mahadevan et al., [Lewis Acid]+[Co(CO)4]—Complexes: A Versatile Class of Catalysts for Carbonylative Ring Expansion of Epoxides and Aziridines. Angew. Chem. Int. Ed. 2002;41(15):2781-4.
Makal et al., Methane storage in advanced porous materials. Chem Soc Rev. Dec. 7, 2012;41(23):7761-79. doi: 10.1039/c2cs35251f.
Maki et al., Electron Paramagnetic Resonance Studies of the Electronic Structures of Bis(maleonitriledithiolato)copper(II), -nickel(III), -cobalt(II), and -rhodium(II) Complexes. J. Am Chem. Soc. Nov. 1964;86(21):4580-7.
Marshall et al., Single-Crystal to Single-Crystal Mechanical Contraction of Metal-Organic Frameworks through Stereoselective Postsynthetic Bromination. J. Am. Chem. Soc. 2015;137:9527-30. Epub Jul. 15, 2015.
Merica et al., Synthesis of nitropolychlorinated dibenzo-p-dioxins (NPCDDs) and their photochemical reaction with nucleophiles. Can. J. Chem. 1995;73:826-35.
Metzger et al., Selective Dimerization of Ethylene to 1-Butene with a Porous Catalyst. ACS Cent. Sci. 2016;2(3):148-53. Epub Feb. 19, 2016. Supporting Information Included.
Mlinar et al., Selective Propene Oligomerization with Nickel(II)-Based Metal-Organic Frameworks. ACS Catal. 2014;4(3):717-21. Epub Jan. 27, 2014.
Mondloch et al., Destruction of chemical warfare agents using metal-organic frameworks. Nat. Mater. 2015;14:512-6. Epub Mar. 16, 2015.
Murtuza et al., Ethylene Polymerization Behavior of Tris(pyrazolyl)borate Titanium(IV) Complexes. Organometallics. 2002;21(9):1882-90. Epub Mar. 28, 2002.
Narayanan et al., Optimization of adsorption processes for climate control and thermal energy storage. Int. J. Heat Mass Transf. Oct. 2014;77:288-300.
Ng et al., Experimental investigation of the silica gel-water adsorption isotherm characteristics. Appl. Therm Eng. 2001;21:1631-42.

Nguyen et al., High Methanol Uptake Capacity in Two New Series of Metal-Organic Frameworks: Promising Materials for Adsorption-Driven Heat Pump Applications. Chem. Mater. 2016;28(17):6243-9. Epub Aug. 8, 2016.
Park et al., Cation-Dependent Intrinsic Electrical Conductivity in Isostructural Tetrathiafulvalene-Based Microporous Metal-Organic Frameworks. J. Am. Chem. Soc. 2015;137(5):1774-7. Epub Jan. 18, 2015.
Park et al., Heterogeneous Epoxide Carbonylation by Cooperative Ion-Pair Catalysis in Co(CO)4—Incorporated Cr-MIL-101. ACS Cent. Sci. 2017;3(5):444-8. Epub Mar. 21, 2017. Supporting Information Included.
Park et al., Single-Ion Li+, Na+, and Mg2+ Solid Electrolytes Supported by a Mesoporous Anionic Cu-Azolate Metal-Organic Framework. J. Am. Chem. Soc. 2017;139(38):13260-3. Epub Sep. 7, 2017.
Petit et al., The role of sulfur-containing groups in ammonia retention on activated carbons. Carbon. Mar. 2010;48(3):654-67.
Petit et al., Toward Understanding Reactive Adsorption of Ammonia on Cu-MOF/Graphite Oxide Nanocomposites. Langmuir. 2011;27(21):13043-51. Epub Oct. 4, 2011.
Pommier et al., Recent Advances in β-Lactone Chemistry. Synthesis. 1993;5:441-59.
Qajar et al., Enhanced ammonia adsorption on functionalized nanoporous carbons. Microporous and Mesoporous Materials. Dec. 1, 2015;218:15-23.
Rieth et al., High and Reversible Ammonia Uptake in Mesoporous Azolate Metal-Organic Frameworks with Open Mn, Co, and Ni Sites. J. Am. Chem. Soc. 2016;138(30):9401-4. Epub Jul. 15, 2016. Supporting Information Included.
Rieth et al., Record Atmospheric Fresh Water Capture and Heat Transfer with a Material Operating at the Water Uptake Reversibility Limit. ACS Cent. Sci. 2017;3(6):668-72. May 24, 2017. Supporting Information Included.
Ristic et al., The performance of small-pore microporous aluminophosphates in low-temperature solar energy storage: the structure-property relationship. Adv Func Mater. 2012;22:1952-7.
Saha et al., Fundamental and application aspects of adsorption cooling and desalination. Appl. Therm. Eng. Mar. 25, 2016;97:68-76.
Schmidt et al., A Readily Synthesized and Highly Active Epoxide Carbonylation Catalyst Based on a Chromium Porphyrin Framework: Expanding the Range of Available β-Lactones. Org. Lett. 2004;6(3):373-6. Epub Jan. 8, 2004.
Schmidt et al., Chromium(III) Octaethylporphyrinato Tetracarbonylcobaltate: A Highly Active, Selective, and Versatile Catalyst for Epoxide Carbonylation. J. Am. Chem. Soc. 2005;127(32):11426-35. Epub Jul. 16, 2005.
Schoenecker et al., Effect of water adsorption on retention of structure and surface area of metal-organic frameworks. Ind Eng Chem Res. 2012;51:6513-6519.
Severn et al., "Bound but Not Gagged" Immobilizing Single-Site α-Olefin Polymerization Catalysts. Chem. Rev. 2005;105:4073-147. Epub Oct. 22, 2005.
Shamir, New synthesis of chromium trichloride tetrahydrofuranate. Inorganica Chimica Acta. Feb. 15, 1989;156(2):163-4.
Speiser et al., Catalytic Ethylene Dimerization and Oligomerization: Recent Developments with Nickel Complexes Containing P,N-Chelating Ligands. Acc. Chem. Res. 2005;38(10):784-93. Epub Sep. 9, 2005.
Stiefel et al., The Myth of Nickel(III) and Nickel(IV) in Planar Complexes. J. Am. Chem. Soc. Jul. 1965;87(13):3016-7.
Stoeckli et al., Specific and non-specific interactions between ammonia and activated carbons. Carbon. 2004;42(8-9):1619-24.
Suh et al., Hydrogen storage in metal-organic frameworks. Chem Rev. 2012;112:782-835.
Sumida et al., Carbon dioxide capture in metal-organic frameworks. Chem Rev. Feb. 8, 2012;112(2):724-81. doi: 10.1021/cr2003272. Epub Dec. 28, 2011.
Svejda et al., Ethylene Oligomerization and Propylene Dimerization Using Cationic (α-Diimine)nickel(II) Catalysts. Organometallics. 1999;18(1):65-74. Epub Dec. 15, 1998.

(56) References Cited

OTHER PUBLICATIONS

Tamainot-Telto et al., Carbon-ammonia pairs for adsorption refrigeration applications: ice making, air conditioning and heat pumping. International Journal of Refrigeration. Sep. 2009;32(6):1212-29.
Tatsidjodoung et al., A review of potential materials for thermal energy storage in building applications. Renew. Sust. Energ. Rev. 2013;18:327-49.
Teufel et al., MFU-4—A Metal-Organic Framework for Highly Effective $H_2/D_2$ Separation. Adv. Mater. Jan. 2013;25(4):635-9.
Theopold, Homogeneous Chromium Catalysts for Olefin Polymerization. Eur. J. Inorg. Chem. Jan. 1998;1:15-24.
Tonigold et al., Pyrazolate-based cobalt(II)-containing metal-organic frameworks in heterogeneous catalytic oxidation reactions: elucidating the role of entatic states for biomimetic oxidation processes. Chemistry. Jul. 25, 2011;17(31):8671-95. doi: 10.1002/chem.201003173. Epub Jun. 17, 2011.
Tulchinsky et al., Reversible Capture and Release of C12 and Br2 with a Redox-Active Metal-Organic Framework. J. Am. Chem. Soc. 2017;139(16):5992-7. Epub Mar. 28, 2017.
Van Humbeck et al., Ammonia Capture in Porous Organic Polymers Densely Functionalized with Brønsted Acid Groups. J. Am. Chem. Soc. 2014;136(6):2432-40. Epub Jan. 23, 2014.
Wade et al., Facile Deposition of Multicolored Electrochromic Metal-Organic Framework Thin Films. Angew Chem. Int. Ed. 2013;52(50):13377-81. Epub Oct. 16, 2013.
Wade et al., Investigation of the synthesis, activation, and isosteric heats of $CO_2$ adsorption of the isostructural series of metal-organic frameworks $M_3(BTC)_2$ (M = Cr, Fe, Ni, Cu, Mo, Ru). Dalton Trans. Jul. 14, 2012;41(26):7931-8. doi: 10.1039/c2dt30372h. Epub Apr. 26, 2012.
Wade et al., Postsynthetic tuning of hydrophilicity in pyrazolate MOFs to modulate water adsorption properties. Energy Environ. Sci. 2013;6:2172-7.
Wade, Designing functionality for anion detection with molecular receptors and small molecule adsorption in microporous materials. PowerPoint Presentation. Brandeis University. Dec. 4, 2012. 50 pages.
Wang et al., A review on adsorption working pairs for refrigeration. Renewable and Sustainable Energy Reviews. Apr. 2009;13(3):518-34.
Wang et al., Pyrazolate-Based Porphyrinic Metal-Organic Framework with Extraordinary Base-Resistance. J. Am. Chem. Soc. 2016;138(3):914-9. Epub Dec. 30, 2015.
Wickenheisser et al., Grafting of hydrophilic ethylene glycols or ethylenediamine on coordinatively unsaturated metal sites in MIL-100(Cr) for improved water adsorption characteristics. Inorganica Chimica Acta. 2013;407:145-52.
Wu et al., A Homochiral Porous Metal-Organic Framework for Highly Enantioselective Heterogeneous Asymmetric Catalysis. J. Am. Chem. Soc. 2005;127(25):8940-1. Epub Jun. 4, 2005.
Wu et al., Adsorption sites and binding nature of $CO_2$ in prototypical metal-organic frameworks: a combined neutron diffraction and first-principles study. J Phys Chem Lett. 2010;1(13):1946-51.
Xiao et al., Oxidation of ethane to ethanol by $N_2O$ in a metal-organic framework with coordinatively unsaturated iron(II) sites. Nat Chem. Jul. 2014;6(7):590-5. doi: 10.1038/nchem.1956. Epub May 18, 2014.
Yamada et al., First-Principles Design of Half-Filled Flat Band of the Kagome Lattice in Two-Dimensinoal Metal-Organic Frameworks. Jul. 26, 2016. arXiv:1510.00164v3.
Yamazoe et al., Receptor Function and Response of Semiconductor Gas Sensor. Journal of Sensors. 2009;2009:21 pages.
Yang et al., Temperature-Triggered Collection and Release of Water from Fogs by a Sponge-Like Cotton Fabric. Adv. Mater. Feb. 25, 2013;25(8):1150-4.
Zhang et al., Ethylene Oligomerization Over Heterogeneous Catalysts. Energy and Environment Focus. Sep. 2014;3(3):246-56.
Achmann et al., Metal-Organic Frameworks for Sensing Applications in the Gas Phase. Sensors. 2009;9(3):1574-89. Epub Mar. 6, 2009.
Bertrand et al., Thiophene-based covalent organic frameworks. PNAS. Mar. 26, 2013;110(13):4923-8. Epub Mar. 11, 2013.
Campbell et al., $Cu_3$(hexaiminotriphenylene)2: An Electrically Conductive 2D Metal-Organic Framework for Chemiresistive Sensing. Angewandte Chemie Int Ed. Mar. 27, 2015;54(14):4349-52. Epub Feb. 9, 2015. Supporting Information Included.
Chen et al., Noncovalently Netted, Photoconductive Sheets with Extremely High Carrier Mobility and Conduction Anisotropy from Triphenylene-Fused Metal Trigon Conjugates. J Am Chem Soc. 2009;131(21):7287-92. Epub May 4, 2009.
Cui et al., An electroactive porous network from covalent metal-dithiolene links. Chem Commun. 2014;50:3986-8. Epub Feb. 24, 2014.
Furukawa et al., The chemistry and applications of metal-organic frameworks. Science. Aug. 30, 2013;341(6149):1230444. doi: 10.1126/science.1230444. 12 pages.
Gandara et al., Porous, Conductive Metal-Triazolates and Their Structural Elucidation by the Charge-Flipping Method. Chem Eur J. Aug. 20, 2012;18(34):10595-601. Epub Jun. 22, 2012.
Gutzler et al., π-Electron Conjugation in Two Dimensions. J Am Chem Soc. 2013;135(44):16585-94. Epub Sep. 19, 2013.
Hao et al., Structurally Designed Synthesis of Mechanically Stable Poly(benzoxazine-co-resol)-Based Porous Carbon Monoliths and Their Application as High-Performance $CO_2$ Capture Sorbents. J Am Chem Soc. 2011;133(29):11378-88. Epub Jun. 21, 2011.
Hmadeh et al., New Porous Crystals of Extended Metal-Catecholates. Chemistry of Materials. 2012;24(18):3511-3. Epub Aug. 28, 2012.
Kambe et al., Redox Control and High Conductivity of Nickel Bis(dithiolene) Complex π-Nanosheet: A Potential Organic Two-Dimensional Topological Insulator. J Am Chem Soc. 2014;136(41):14357-60. Epub Sep. 24, 2014.
Kambe et al., π-Conjugated Nickel Bis(dithiolene) Complex Nanosheet. J Am Chem Soc. 2013;135(7):2462-5. Epub Jan. 29, 2013.
Kobayashi et al., Conductivity, Doping, and Redox Chemistry of a Microporous Dithiolene-Based Metal-Organic Framework. Chem Mater. 2010;22(14):4120-2. Epub Jun. 25, 2010.
Kong et al., Opportunities in chemistry and materials science for topological insulators and their nanostructures. Nature Chemistry. 2011;3:845-9. Epub Oct. 24, 2011.
Kreno et al., Metal-Organic Framework Materials as Chemical Sensors. Chemical Reviews. 2012;112(2):1105-25. Epub Nov. 9, 2011.
Miner et al., Electrochemical oxygen reduction catalysed by $Ni_3$(hexaiminotriphenylene)2. Nat Commun. Mar. 2016:7:10942. 7 pages.
Narayan et al., High Charge Mobility in a Tetrathiafulvalene-Based Microporous Metal-Organic Framework. J Am Chem Soc. 2012;134(31):12932-5. Epub Jul. 24, 2012.
Sheberla et al., Conductive MOF electrodes for stable supercapacitors with high areal capacitance. Nature Materials. 2017;16:220-4. Epub Oct. 10, 2016. Supporting Information Included.
Sheberla et al., High Electrical Conductivity in $Ni_3(2,3,6,7,10,11$-hexaiminotriphenylene)2, a Semiconducting Metal-Organic Graphene Analogue. J Am Chem Soc. 2014;136(25):8859-62. Epub Apr. 21, 2014. Supporting Information Included.
Shustova et al., Selective Turn-On Ammonia Sensing Enabled by High-Temperature Fluorescence in Metal-Organic Frameworks with Open Metal Sites. J Am Chem Soc. 2013;135(36):13326-9. Epub Aug. 27, 2013.
Stavila et al., MOF-based electronic and opto-electronic devices. Chem Soc Rev. Aug. 21, 2014;43(16):5994-6010. doi: 10.1039/c4cs00096j.
Sun et al., Electrically Conductive Porous Metal-Organic Frameworks. Angew Chem Int Ed Engl. Mar. 7, 2016;55(11):3566-79. doi: 10.1002/anie.201506219. Epub Jan. 8, 2016. Review.
Sun et al., Measuring and Reporting Electrical Conductivity in Metal-Organic Frameworks: $Cd_2$(TTFTB) as a Case Study. J Am Chem Soc. 2016;138(44):14772-82. Epub Oct. 21, 2016.
Sun et al., $Mn_2(2,5$-disulthydrylbenzene-1,4-dicarboxylate): A Microporous Metal-Organic Framework with Infinite (-Mn—S-)∞Chains and High Intrinsic Charge Mobility. J Am Chem Soc. 2013;135(22):8185-8. Epub May 14, 2013.

(56) References Cited

OTHER PUBLICATIONS

Talin et al., Tunable electrical conductivity in metal-organic framework thin-film devices. Science. Jan. 3, 2014;343(6166):66-9. doi: 10.1126/science.1246738. Epub Dec. 5, 2013.
Wang et al., Organic topological insulators in organometallic lattices. Nat Commun. 2013;4:1471. Epub Feb. 12, 2013. 5 pages.
Wang et al., Prediction of a Two-Dimensional Organic Topological Insulator. Nano Lett. 2013;13(6):2842-5. Epub May 16, 2013.

* cited by examiner

COMPOSITIONS AND METHODS COMPRISING CONDUCTIVE METAL ORGANIC FRAMEWORKS AND USES THEREOF

RELATED APPLICATIONS

This application is a national stage application under 35 U.S.C. § 371 of International Patent Application Serial No. PCT/US2015/029503, filed May 6, 2015, entitled "COMPOSITIONS AND METHODS COMPRISING CONDUCTIVE METAL ORGANIC FRAMEWORKS AND USES THEREOF," which claims priority to and the benefit of, and incorporates herein by reference in its entirety U.S. provisional patent applications, U.S. Ser. No. 61/988,952, filed May 6, 2014, entitled "COMPOSITIONS AND METHODS COMPRISING CONDUCTIVE METAL ORGANIC FRAMEWORKS AND USES THEREOF" and U.S. Ser. No. 62/091,100, filed Dec. 12, 2014, entitled "COMPOSITIONS AND METHODS COMPRISING CONDUCTIVE METAL ORGANIC FRAMEWORKS AND USES THEREOF," each of which is incorporated herein by reference their entirety.

GOVERNMENT FUNDING

This invention was made with Government support under Grant Nos. DE-SC0006937 and DE-SC0001088 awarded by the Department of Energy. The Government has certain rights in the invention.

FIELD

Compositions and methods comprising metal organic frameworks (MOFs) and related uses are generally provided. In some embodiments, a MOF comprises a plurality of metal ions, each coordinated with at least one ligand comprising at least two sets of ortho-diimine groups arranged about an organic core.

BACKGROUND

Two-dimensional (2D) electronic materials are of considerable interest due to their potential applications in future electronics. A common example is graphene, a thin organic 2D material with in-plane π-conjugation. Although graphene exhibits exceptional charge mobility and mechanical stability, its use in semiconductor-based devices is limited by its zero bandgap. Dimensional reduction and chemical functionalization can increase the bandgap, rendering graphene semiconducting, but such methods generally reduce its charge mobility and can introduce numerous defects. This has led to a sustained effort towards identifying 2D materials with intrinsic non-zero bandgaps that could replace conventional semiconductors. Two other broad classes of materials have been investigated: the layered metal chalcogenides (e.g., $MoS_2$, $WSe_2$) and 2D covalent-organic frameworks (COFs). The former can be deposited as large-area single sheets in a "top-down" approach. They have been shown to perform well in device testing, but do not easily lend themselves to chemical functionalization and tunability. In contrast, COFs generally are prepared by "bottom-up" solution-based synthetic methods.

While COFs are attractive because they are subject to rational modification, the electronic properties of COFs are largely inferior to metal chalcogenides because the functional groups used to connect their building blocks typically do not allow in-plane conjugation.

Accordingly, improved compositions and methods are needed.

SUMMARY

In some embodiments, a metal organic framework is provided comprising a plurality of metal ions, each coordinated with at least one ligand comprising at least two sets of ortho-diimine groups arranged about an organic core.

In some embodiments, a method of synthesizing a porous metal organic framework (MOF) is provided comprising exposing a plurality of metal ions to a plurality of precursor ligands in the presence of an oxidant and a base to form a MOF comprising a portion of the plurality of metal ions each coordinated with at least one ligand, wherein each ligand comprises at least two sets of ortho-diimine groups arranged about an organic core.

Figure 1:
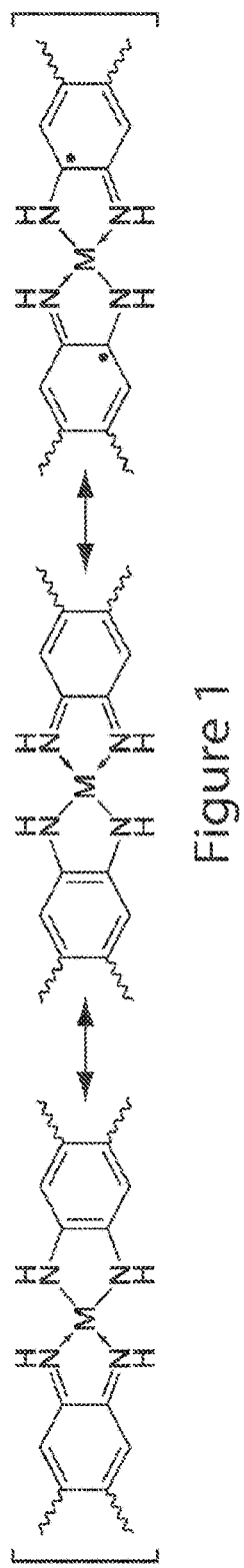
FIG. 1 shows a non-limiting example of a MOF, according to some embodiments.

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

Compositions and methods comprising metal organic frameworks (MOFs) and related uses are generally provided. In some embodiments, a MOF comprises a plurality of metal ions, each coordinated with at least one ligand comprising at least two sets of ortho-diimine groups arranged about an organic core.

The term "metal-organic framework" is given its ordinary meaning in the art and refers to a one-, two-, or three-dimensional coordination polymer including metal ions and ligands which function as organic structural units, wherein a portion of the metal ions are each chemically bonded to at least one bi-, tri- or poly-dentate ligand. The metal ions, in addition to being coordinated with at least one organic structure unit, may also be bound to one or more auxiliary ligands, as described in more detail herein.

In some embodiments, a MOF comprises a plurality of metal ions, each coordinated with at least one ligand comprising at least two sets of ortho-diimine groups arranged about an organic core. In some embodiments, the at least one ligand comprises at least two ortho-phenylenediimine units. In some embodiments, a portion of the metal ions are associated with two, three, or four ligands, and each of those ligand is individually associated with one, two, three, or four metal ions. In some embodiments, a portion of the metal ions are associated with two ligands, and each of those ligands is individually associated with two metal ions. In some embodiments, a portion of the metal ions are associated with three ligands, and each of those ligands is individually associated with three metal ions. In some embodiments, a portion of the metal ions are associated with two ligands, and each of those ligands is individually associated with three metal ions. In some embodiments, a ligand is charged. In some embodiments, a ligand has a charge of (−1), or (−2), or (−3), or (−4). In some embodiments, a ligand has a charge of (−2).

In some embodiments, each ligand comprises two sets of ortho-diimine groups. In some embodiments, each ligand comprising two sets of ortho-diimine groups may be associated with two metal atoms. In some embodiments, each ligand comprises three sets of ortho-diimine groups. In some embodiments, each ligand comprising three sets of ortho-diimine groups may be associated with three metal atoms. In some embodiments, each ligand comprises four sets of ortho-diimine groups. In some embodiments, each ligand comprising four sets of ortho-diimine groups may be associated with four metal atoms.

In some embodiments, the at least one ligand comprises at least two sets of ortho-phenylenediimine units. In some embodiments, the at least one ligand comprises two sets of ortho-phenylenediimine units. In some embodiments, the at least one ligand comprises three sets of ortho-phenylenediimine units. In some embodiments, the at least one ligand comprises four sets of ortho-phenylenediimine units.

The organic core comprising at least two set of ortho-diimine groups may be any suitable core. In some embodiments, the core is aromatic. Generally, the core comprises a rigid structure formed from fused aryl and/or heteroaryl rings. In some embodiments, the organic core comprises a plurality of fused aryl and/or heteroaryl rings. In some cases, the organic core comprises a plurality of fused aryl rings. In some cases, the organic core comprises one or more of benzyl, thiophenyl, carbazolyl, pyrrolyl, indolyl, and furanyl rings.

In some embodiments, the at least one ligand comprising at least two sets of ortho-diimine groups arranged about an organic core comprises the structure:

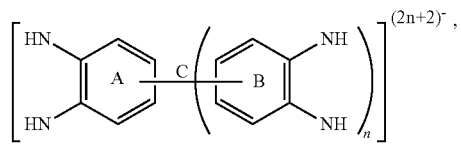

wherein n is 1, 2, or 3, and C represent one or more bonds formed between ring A and each ring B. In some cases, n is 1. In some cases, n is 2. In some cases, n is 3.

In some embodiments, the at least one ligand comprises the structure:

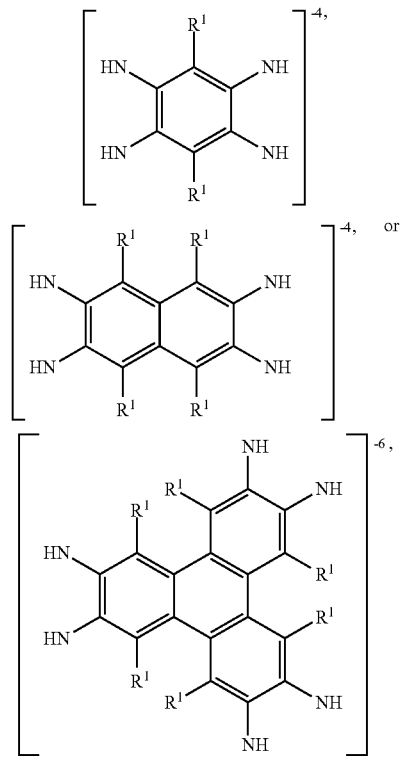

wherein each $R^1$ is the same or different and is selected from the group consisting of hydrogen, $-NO_2$, $-R'$, $-F$, $-Cl$, $-Br$, $-I$, $-CN$, $-NC$, $-SO_3R'$, $-SO_3H$, $-OR'$, $-OH$, $-SR'$, $-SH$, $-PO_3R'$, $-PO_3H$, $-CF_3$, $-NR'_2$, $-NHR'$, and $-NH_2$, wherein each R' is the same or different and is optionally substituted alkyl or optionally substituted aryl. In some embodiments, the at least one ligand comprises the structure:

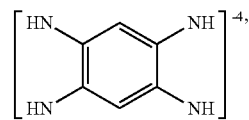

-continued
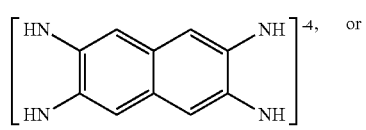
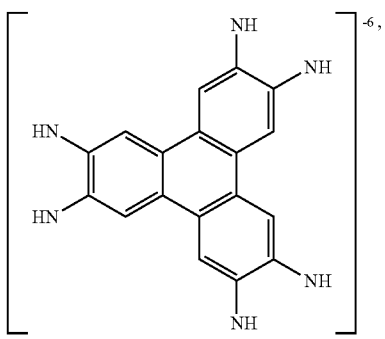
Other non-limiting examples of ligands include:
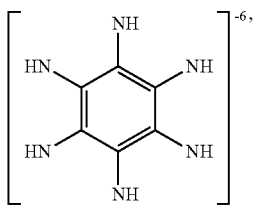
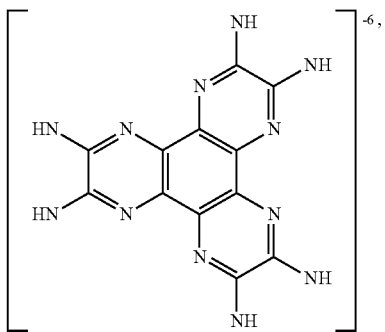
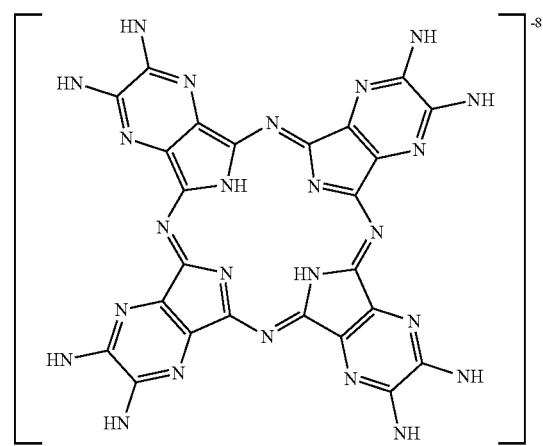
-continued
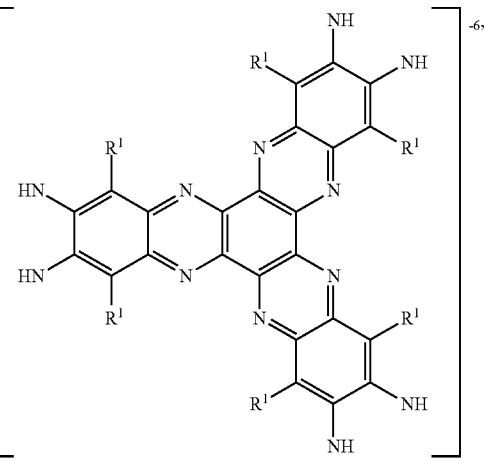
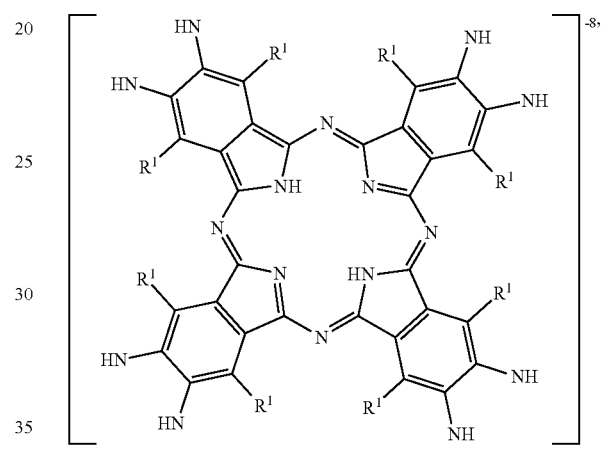
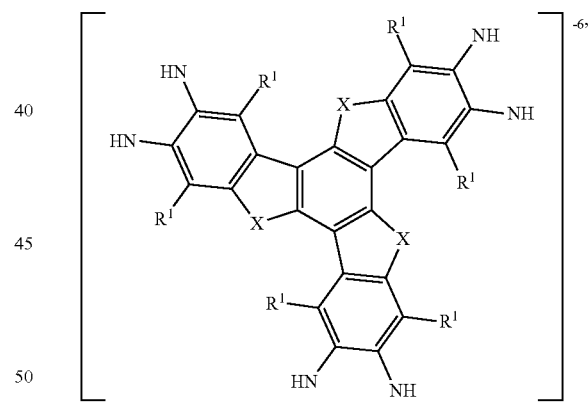
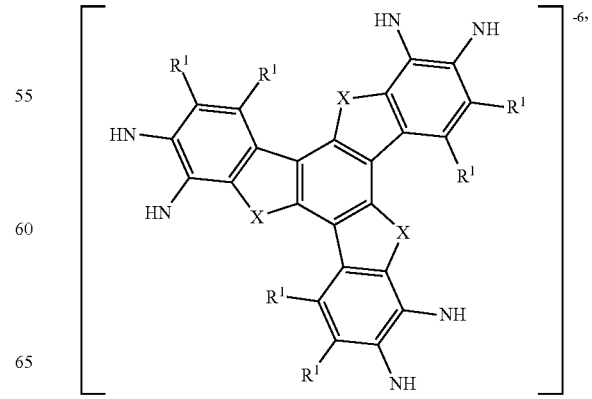

-continued

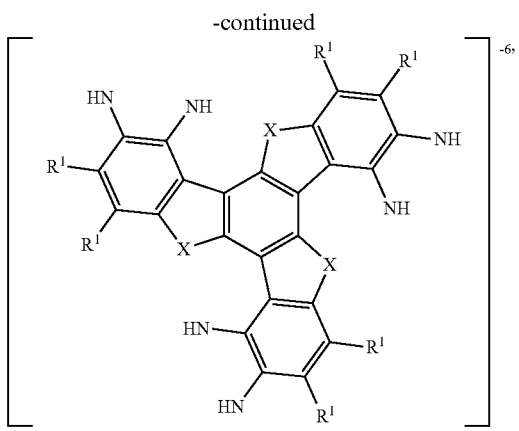

wherein each R¹ is the same or different and is selected from the group consisting of hydrogen, —NO₂, —R', —F, —Cl, —Br, —I, —CN, —NC, —SO₃R', —SO₃H, —OR', —OH, —SR', —SH, —PO₃R', —PO₃H, —CF₃, —NR'₂, —NHR', and —NH₂; each X is the same or different and is selected from the group consisting of NR', O, S, Se, and Te; and each R' is the same or different and is optionally substituted alkyl or optionally substituted aryl. In some embodiments, each R¹ is hydrogen. In some embodiments, each X is the same or different and is selected from the group consisting of NR', O and S. In some embodiments, each X is NR'. In some embodiments, each X is O. In some embodiments, each X is S. In some embodiments, each X is Se. In some embodiments, each X is Te. In some embodiments, each R' is H.

In some embodiments, more than one type of ligand may be employed, for example, a first type of ligand and a second type of ligand. The two or more types of ligands may be provided in any suitable ratio. The two or more types of ligands may be provided in any suitable ratio.

Any suitable metal ion may be employed. Each metal ion may be a monovalent, divalent, or trivalent. In some embodiments, each metal ion is a monovalent metal ion. Non-limiting examples of monovalent metal ions are Ag⁺, Cu⁺, and Au⁺. In some cases, the metal ion is Cu⁺. In some embodiments, the metal ion is a divalent metal ion. Non-limiting examples of monovalent metal ions are Mg²⁺, Mn²⁺, Fe²⁺, Co²⁺, Ni²⁺, Cu₂₊, Pd²⁺, Pt²⁺, Ru²⁺, Cd²⁺, Zn²⁺, Pb²⁺, Hg²⁺, V²⁺, Cr²⁺, and Ni⁺². In some cases, the metal ion is Ni⁺². In some cases, the metal ion is Cu²⁺. In some embodiments, the metal ion is a trivalent metal ion. Non-limiting examples of trivalent metal ions are Fe³⁺, V³⁺, Ti³⁺, Sc³⁺, Al³⁺, In³⁺, Ga³⁺, Mn³⁺, Co³⁺, and Cr³⁺. In some embodiments, a metal organic framework (MOF) may comprise two or more metal ions having a different valency. For example, the metal organic framework may comprise one or more monovalent metal ion and one or more divalent metal ion. In some such embodiments, the one or more ligand may be redox active and/or able to accommodate the different redox states of the metal ion. In some embodiments, the one or more metal ions may be the same metal ion but in different redox states (e.g., Cu⁺ and Cu⁺²).

In some embodiments, more than one type of metal ion may be employed, for example, a first type of metal ion and a second type of metal ion. In some cases, the first type of metal ion and the second type of metal ion have the same valency. For example, the first type of metal ion may be a first type divalent metal ion and the second type of metal ion may be a second type of divalent metal ion. The two or more types of metal ions may be provided in any suitable ratio.

In some embodiments, a metal ion may be associated with one or more auxiliary ligands. In some cases, the one or more auxiliary ligands may be found above and/or below the metal ion (e.g., as apical ligands). An auxiliary ligand may or might not be charged. Non-limiting examples of auxiliary ligands include halides (e.g., chlorine, fluorine, bromine, iodine), other salts (e.g., nitrate, carbonate, sulfonate, etc.), and coordinating solvents (e.g., water, pyridine, tetrahydrofuran, diethyl ether, etc.).

In some embodiments, methods of synthesis are provided. In some cases, a method of synthesizing a MOF comprises exposing a plurality of metal ions to a plurality of precursor ligands in the presence of an oxidant and a base to form a MOF comprising a portion of the plurality of metal ions each coordinated with at least one ligand, wherein each ligand comprises at least two sets of ortho-diimine groups arranged about an organic core. Non-limiting examples of ligands comprises at least two sets of ortho-diimine groups arranged about an organic core are described herein. In some embodiments, the metal ion is provided as a salt, and the at least one precursor ligand provided comprises at least two sets of ortho-diamine groups. During the course of the reaction, the diamine groups of the precursor ligand are oxidized into the corresponding diimine group, which coordinates with a metal ion. In some cases, the precursor ligand comprises at least two sets of ortho-phenylenediamine groups, and during the course of the reaction, the precursor ligand is oxidized so that each ortho-phenylenediamine group is transformed into an ortho-phenylenediimine group, which coordinates with a metal ion.

The metal ion and the precursor ligand may be provided in any suitable amounts. In some embodiments, the mole ratio of the metal ion to the precursor ligand may be based upon the coordination of the metal ion to the ligand. For example, in embodiments where the ligand is coordinated with three metal ions, and each metal ion is associated with two ligands, the mole ratio of the metal ion to the precursor ligand may be about least 3:2. As another example, in embodiments, where the ligand is coordinated with two metal ions, and each metal ion is associated with one ligand, the mole ratio of the metal ion to the precursor ligand may about 2:1. In some embodiments, the precursor ligand is providing in slight mole excess as compared to the metal ion.

In some embodiments, the metal ions are provided as a salt. Non-limiting examples of salts chloride, fluoride, bromide, iodide, triflate, BF₄, PF₆, NO₃⁻, SO₄²⁻, and ClO₄⁻ salts. In some cases, the salt is SO₄²⁻.

In some embodiments, the at least one precursor ligand comprising at least two sets of ortho-diamine groups arranged about an organic core comprises the structure:

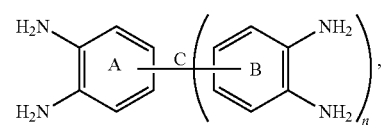

wherein n is 1, 2, or 3, and C represent one or more bonds formed between ring A and each ring B. In some cases, n is 1. In some cases, n is 2. In some cases, n is 3

In some embodiments, the at least one precursor ligand comprises the structure:

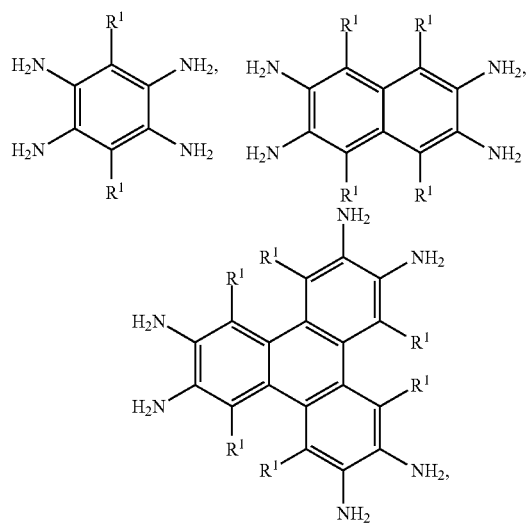

wherein each $R^1$ is the same or different and is selected from the group consisting of hydrogen, $-NO_2$, $-R'$, $-F$, $-Cl$, $-Br$, $-I$, $-CN$, $-NC$, $-SO_3R'$, $-SO_3H$, $-OR'$, $-OH$, $-SR'$, $-SH$, $-PO_3R'$, $-PO_3H$, $-CF_3$, $-NR'_2$, $-NHR'$, and $-NH_2$, wherein each R' is the same or different and is optionally substituted alkyl or optionally substituted aryl. In some embodiments, the at least one precursor ligand comprises the structure:

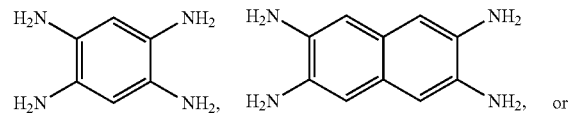

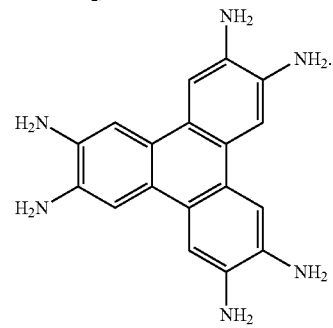

Other non-limiting examples of precursor ligands include:

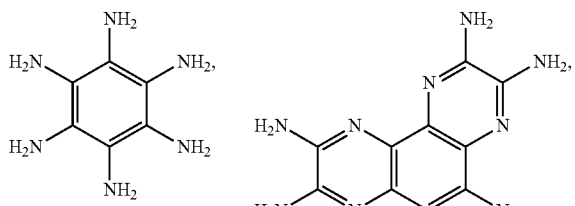

-continued

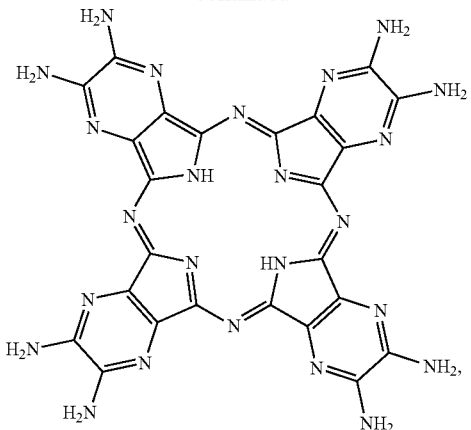

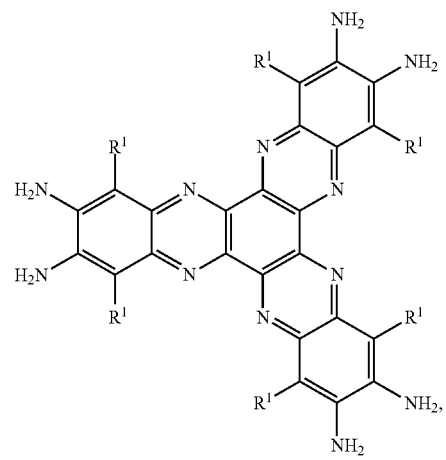

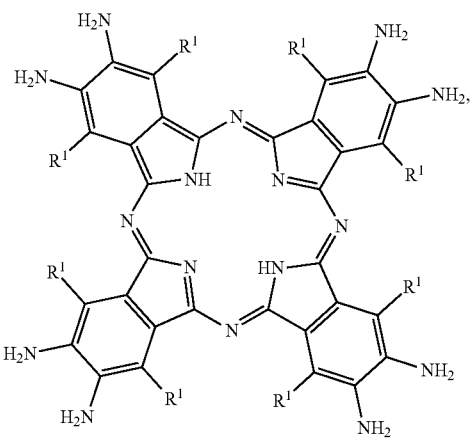

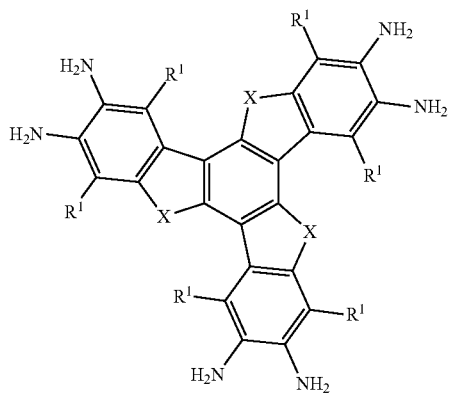

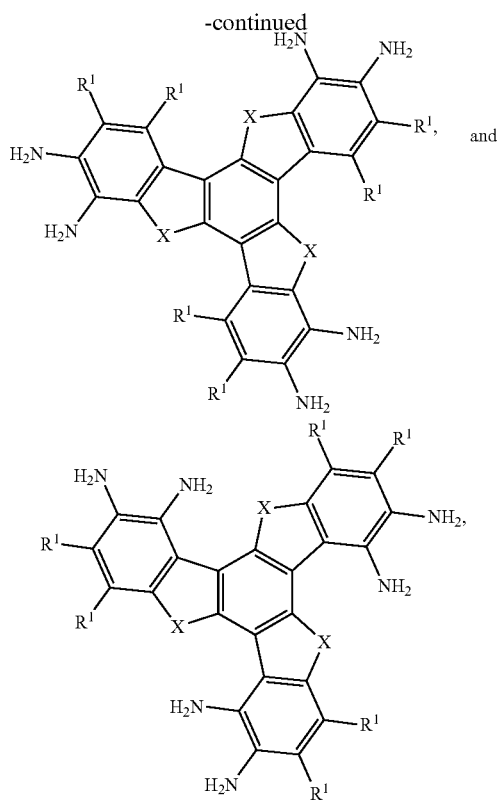

wherein each $R^1$ is the same or different and is selected from the group consisting of hydrogen, —$NO_2$, —R', —F, —Cl, —Br, —I, —CN, —NC, —$SO_3R'$, —$SO_3H$, —OR', —OH, SR', —SH, —$PO_3R'$, —$PO_3H$, —$CF_3$, —$NR'_2$, —NHR', and —$NH_2$; each X is the same or different and is selected from the group consisting of NR', O, S, Se, and Te; and each R' is the same or different and is optionally substituted alkyl or optionally substituted aryl. In some embodiments, each $R^1$ is hydrogen. In some embodiments, each X is the same or different and is selected from the group consisting of NR', O, and S. In some embodiments, each X is NR'. In some embodiments, each X is O. In some embodiments, each X is S. In some embodiments, each X is Se. In some embodiments, each X is Te. In some embodiments, each R' is H.

Any suitable base may be utilized in the synthetic methods described herein. Non-limiting examples of bases include NR"$_3$ wherein each R" is the same or different and is hydrogen, optionally substituted alkyl, or optionally substituted aryl; QOH, wherein Q is a cation (e.g., a metal cation, a semi-metal cation, $NH_4$); acetate. In some embodiments, the base is $NH_3$ or $NH_4OH$. In some embodiments, the base is selected to have a higher pH as compared to the amino groups on the precursor ligand.

Any suitable oxidant may be employed. In some embodiments, the oxidant is oxygen. In some embodiments, the oxidant is a chemical oxidant. Non-limiting examples of oxidants include air, oxygen, ferricinium, nitrosonium, $Ag^{2+}$, $Ag^+$, $Fe^{+3}$, $MnO_4^-$, and $CrO_4^-$. The oxidant may be present in an amount suitable to aid in the oxidation of the precursor ligand. In some embodiments, the oxidant is present in excess.

Any suitable solvent may be utilized in the synthetic methods described herein. Non-limiting examples of solvents include water, methanol, ethanol, propanol, benzene, p-cresol, toluene, xylene, diethyl ether, glycol, diethyl ether, petroleum ether, hexane, cyclohexane, pentane, methylene chloride, chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, mixtures thereof, or the like. In some embodiments, the solvent is water.

The methods of synthesis described herein may be carried out at any suitable temperature. In some cases, the reaction is carried out at about room temperature (e.g., about 25° C., about 20° C., between about 20° C. and about 25° C., or the like). In some cases, however, the reaction is carried out at temperatures below or above room temperature. In some embodiments, the reaction is carried at a temperature between about 25° C. and about 100° C., or between about 35° C. and about 95° C., or between about 45° C. and about 85° C., or between about 55° C. and about 75° C.

MOFs synthesized using the methods described herein may be purified using techniques known to those of ordinary skill in the art. In some embodiments, a synthesized MOF may be washed, sometimes involving a Soxhlet extractor, boiled, and/or sonicated (e.g., to remove excess starting materials).

The synthetic methods described herein may provide for rapid synthesis of a wide range of MOFs. The ability to synthesize MOFs rapidly may be useful for the screening of known, as well as new MOFs, to determine the conductivity of the MOF.

The MOFs, in some cases, may be formed as a film on a surface of a material. The film may be formed using techniques known to those of ordinary skill in the art. For example, the film may be formed by spin-casting method, drop-casting method, dip coating method, roll coating method, screen coating method, a spray coating method, screen printing method, ink-jet method, and the like. In some cases, the thickness of the film may be less than about 100 um (micrometer), less than about 10 um, less than about 1 um, less than about 100 nm, less than about 10 nm, less than about 1 nm, or thinner. In some cases, the film may have a thickness greater than 1 mm. In some embodiments, the substrate on which the film is formed may be a conductive. For example, the substrate may comprise quartz, indium-tin-oxide coated glass, silicon wafer, etc.

In some embodiments, the MOFs formed (e.g., a film of an MOF) may comprise little or no excess metal ions. That is, the MOF comprises essentially no metal ions which are not coordinated with a ligand comprising at least two ortho-diimine groups (i.e., "free metal ions"). In some embodiments, the MOF comprises less than about 0.5 wt %, or less then about 0.4 wt %, or less then about 0.3 wt %, or less than about 0.2 wt %, or less then about 0.1 wt %, or less than about 0.05 wt %, or less than about 0.03 wt %, or less than about 0.02 wt %, or less than about 0.01 wt %, or less than about 0.005 wt %, or less than about 0.001 wt % of free metal ions. Those of ordinary skill in the art will be aware of methods for determining the amount of free metal ions, for example, using XPS (e.g., see Example 1).

The MOFs described herein or the MOFs synthesized using the methods described herein may be utilized in a wide variety of applications. In some embodiments, the MOFs described herein are conductive. In such embodiments, the MOFs may be employed in applications in the semiconductor, chemical, and/or electronics industries. Non-limiting examples of such applications include electrochemical sensors, electrocatalysts, and electronic devices (e.g., light-emitting diodes, photovoltaic solar cells, and transistors). In some cases, the substituents of the ligands (e.g., comprising at least two sets of ortho-diamine units) may be tuned to provide the desired properties. As the molecular building blocks can be changed by synthetic manipulations and/or by changing the metal precursor, the MOFs described herein have variable electrical conductivity that can be tuned to be suitable for one or more of the applications described herein.

In some embodiments, the MOFs may be used for chemical sensing. The MOFs, in some instances, may be used to detect the presence, absence, and/or concentration of one or more target analytes. For instance, a MOF, described herein, comprising a metal ion (e.g., $Cu^{2+}$) may be used to detect a target analyte, such as ammonia (e.g., in the vapor phase). In some embodiments, a MOF device for chemical sensing may comprise a porous metal organic framework comprising a plurality of metal ions, each coordinated with at least one ligand comprising at least two sets of ligands (e.g., ortho-diimine groups) arranged about a core (e.g., organic core) on an substrate (e.g., electrically conductive and/or optically transparent substrate). In some embodiments, the MOF may be deposited on the substrate, such that the MOF is in direct physical contact with the substrate. In other embodiments, the MOF may not be in direct physical contact with the substrate. In some embodiments, the plurality of metal ions may be selected based on their ability to interact with the target analyte. In certain embodiments, substantially the same ligands may be used with different metal ions to detect a variety of target analytes.

In general, MOF chemical sensors may be used to detect a target analyte in or contained in a material in any phase. For example, the target analyte may be in or carried in a material in the liquid and/or vapor phase. In some such embodiments, a MOF chemical sensing device is exposed to the liquid and/or vapor comprising the target analyte. The target analyte may interact with, e.g., one or more metal ions in the MOF. The interaction between the metal ion and target analyte may detectably alter one or more chemical and/or physical property of the MOF. Any suitable detector may be used to detect a physical and/or chemical change of the MOF due to interaction with the target analyte. In some embodiments, the detection of the target analyte(s) may be based on an electrochemical or resistance measurement using, e.g., a potentiostat. Those of ordinary skill in the art would be knowledgeable of suitable detectors. In some embodiments, the target analyte is ammonia. Other non-limiting examples of target analytes include $O_2$ (e.g., for combustion monitoring, safety), $CO_2$ (e.g., for safety, property management, produce monitoring), CO (e.g., for safety), oxides of nitrogen (e.g., for safety, environmental monitoring), water (e.g., for monitoring), amines (e.g., for safety), N-heterocycles (e.g., for safety), alcohols (e.g., breath anlaysis), ketones (e.g., for breath analysis, explosives detection), aldehydes (e.g., for indoor air quality), ethers (e.g., for safety), aromatics (e.g., for safety), nitriles (e.g., for safety), phosphonates (e.g., for chemical warfare agents), hydrocarbons (e.g., olefins such as ethylene for produce monitoring and food industry).

In some embodiments, the MOFs are conductive. Those of ordinary skill in the art will be aware of methods to determine the conductivity of an MOF. For example, as described in the examples, the electrical conductivity of an MOF may be measured in polycrystalline pellet form and/or in polycrystalline film form. In some cases, a pellet of an MOF may be compressed between two steel rods and subjected to a two-probe direct current measurement. In some embodiments, the conductivity of a MOF in pellet form is at least about 1 $S·cm^{-1}$, or at least about 1.5 $S·cm^{-1}$, or at least about 2 $S·cm^{-1}$, or at least about 2.5 $S·cm^{-1}$, or between about 1 $S·cm^{-1}$ and about 10 $S·cm^{-1}$, or between about 1 $S·cm^{-1}$ and about 7 $S·cm^{-1}$, or between about 1 $S·cm^{-1}$ and about 5 $S·cm^{-1}$, or between about 2 $S·cm^{-1}$ and about 10 $S·cm^{-1}$, or between about 2 $S·cm^{-1}$ and about 7 $S·cm^{-1}$, or between about 2 $S·cm^{-1}$ and about 5 $S·cm^{-1}$.

In some embodiments, the conductivity of an MOF in film having an average thickness of about 500 nm is at least about 10 $S·cm^{-1}$, at least about 15 $S·cm^{-1}$, or at least about 20 $S·cm^{-1}$, or at least about 25 $S·cm^{-1}$, or at least about 30 $S·cm^{-1}$, or at least about 35 $S·cm^{-1}$, or at least about 40 $S·cm^{-1}$, or between about 1 $S·cm^{-1}$ and about 100 $S-cm^{-1}$, or between about 1 $S·cm^{-1}$ and about 90 $S·cm^{-1}$, or between about 1 $S·cm^{-1}$ and about 80 $S·cm^{-1}$, or between about 1 $S·cm^{-1}$ and about 70 $S·cm^{-1}$, or between about 1 $S·cm^{-1}$ and about 60 $S·cm^{1}$, or between about 1 $S·cm^{-1}$ and about 50 $S·cm^{-1}$, or between about 1 $S·cm^{-1}$ and about 40 $S·cm^{-1}$, or between about 1 $S·cm^{-1}$ and about 30 $S·cm^{-1}$, or between about 1 $S·cm^{-1}$ and about 20 $S-cm^{-1}$, or between about 1 $S·cm^{-1}$ and about 10 $S·cm^{-1}$, or between about 1 $S·cm^{-1}$ and about 7 $S·cm^{-1}$, or between about 1 $S·cm^{-1}$ and about 5 $S·cm^{-1}$, or between about 2 $S·cm^{-1}$ and about 10 $S·cm^{-1}$, or between about 2 $S·cm^{-1}$ and about 7 $S·cm^{-1}$, or between about 2 $S·cm^{-1}$ and about 5 $S·cm^{-1}$. Other ranges are possible. In some cases, the conductivity is measured at room temperature (e.g., about 25° C.). In some cases, the conductivity may have a linear dependence with temperature.

In some embodiments, the bandgap of the MOF may be varied, e.g., by changing the substituents about the ligand core. Those of ordinary skill in the art will be aware of methods to determine the bandgap of a material, for example, optically or through analytical techniques such as UV photoelectron spectroscopy. In some embodiments, the bandgap of an MOF is between about ~0.3 eV and about ~2.0 eV. Other ranges are possible.

In some embodiments, the charge mobility of the MOF may be varied, e.g., by changing the substituents about the ligand core. Those of ordinary skill in the art will be aware of methods to determine the charge mobility of a material, for example, via a field-effect transistor, Hall measurement, and/or a time-of-flight technique. In some embodiments, the charge mobility is least about 0.1 $cm^2·V^{-1}·s^{-1}$, or at least about 0.5 $cm^2·V^{-1}·s^{-1}$, or at least about 1 $cm^2·V^{-1}·s^{-1}$, or at least about 2 $cm^2·V^{-1}·s^{-1}$, or at least about 3 $cm^2·V^{-1}·S^{-1}$, or at least about 4 $cm^2·V^{-1}·s^{-1}$, or between about 0.1 and about 30 $cm^2·V^{-1}·s^{-1}$, or between about 0.1 and about 20 $cm^2·V^{-1}·s^{-1}$, or between about 0.1 and about 10 $cm^2·V^{-1}·s^{-1}$, or between about 0.1 and about 5 $cm^2·V^{-1}·s^{-1}$, or between about 1 and about 1000 $cm^2·V^{-1}·s^{-1}$, or between about 1 and about 500 $cm^2·V^{-1}·s^{-1}$, or between about 1 and about 250 $cm^2·V^{-1}·s^{-1}$, or between about 1 and about 100 $cm^2·V^{-1}·s^{-1}$, or between about 1 and about 75 $cm^2·V^{-1}·s^{-1}$, or between about 1 and about 50 $cm^2·V^{-1}·s^{-1}$, or between about 1 and about 30 $cm^2·V^{-1}·s^{-1}$, or between about 1 and about 20 $cm^2·V^{-1}·s^{-1}$, or between about 1 and about 10 $cm^2·V^{-1}·s^{-1}$, or between about 1 and about 5 $cm^2·V^{-1}·s^{-1}$, or between about 2 and about 30 $cm^2·V^{-1}·s^{-1}$, or between about 2 and about 20 $cm^2·V^{-1}·s^{-1}$, or between about 2 and about 10 $cm^2·V^{-1}·s^{-1}$, or between about 2 and about 5 $cm^2·V^{-1}·s^{-1}$. In some embodiments, the charge mobility may be determined using an MOF formed as a single sheet with little or no defects.

In some embodiments in which the MOFs are conductive, the MOFs may be used in an electrochemical capacitor. For instance, in some embodiments, a MOF, described herein, comprising a metal ion (e.g., $Ni^{2+}$) may be used as an active material in one or more electrodes of an electrochemical capacitor (e.g., electric double layer supercapacitor, pseudocapacitance supercapacitor). In some such embodiments, the electrochemical capacitors (e.g., supercapacitor) may comprise two electrodes separated by a porous separator (e.g., membrane, fibrous material), and an electrolyte. At least one electrode (e.g., two electrodes) may comprise one or more MOFs. In some instances, the active material in one or more electrodes (e.g., two electrodes) may consist essentially of one or more MOFs. In other instances, the electrode may comprise other active material in addition to one or more MOFs.

As used herein, a supercapacitor has its ordinary meaning in the art and may refer to a capacitor whose active material has a gravimetric capacitance at least 10 $F \cdot g^{-1}$, minimum operating voltage of 1 V, and retains 85% of its capacitance for at least 1,000 cycles.

In some embodiments, an electrochemical capacitor comprising one or more MOFs may have a relatively high gravimetric capacitance. For instance, in such an electrochemical capacitor one or more electrodes may have a specific capacitance of at least about 50 $F \cdot g^{-1}$ (e.g., at least about 70 $F \cdot g^{-1}$, at least about 100 $F \cdot g^{-1}$, at least about 150 $F \cdot g^{-1}$, at least about 200 $F \cdot g^{-1}$) at operating voltage 2 V and current density 1 $A \cdot g^{-1}$. In some instances, the capacitance may be between about 50 $F \cdot g^{-1}$ and about 250 $F \cdot g^{-1}$, between about 70 $F \cdot g^{-1}$ and about 250 $F \cdot g^{-1}$, between about 100 $F \cdot g^{-1}$ and about 250 $F \cdot g^{-1}$, between about 100 $F \cdot g^{-1}$ and about 160 $F \cdot g^{-1}$, between about 50 $F \cdot g^{-1}$ and about 160 $F \cdot g^{-1}$, between about 70 $F \cdot g^{-1}$ and about 150 $F \cdot g^{-1}$, or between about 50 $F \cdot g^{-1}$ and about 100 $F \cdot g^{-1}$.

In some embodiment, an electrochemical capacitor comprising one or more MOFs may have a relatively low time constant. For instance, the time constant may be less than or equal to about 10 seconds, less than or equal to about 8 seconds, less than or equal to about 5 seconds, or less than or equal to about 3 seconds. In some instances, the time constant may be between about 0.5 seconds and about 10 seconds, between about 0.5 seconds and about 8 seconds, between about 0.5 seconds and about 5 seconds, or between about 0.5 seconds and about 3 seconds. One of ordinary skill in the art would be knowledgeable of methods to determine the time constant. The time constant may be determined using electrochemical impedance spectroscopy. Briefly, from the electrochemical impedance data, the imaginary capacitance may be determined as a function of frequency. The reciprocal of the frequency $f_0$ of a local maximum in the data yields a time constant. The electrochemical impedance may be determined at 22° C. in 1.5M tetraethyl ammonium tetra-fluoroborate ($TEABF_4$) in acetonitrile electrolyte solution having a density of 0.89 $g/cm^3$. The current collector may have good contact with the electrodes during the measurement. In some instances, a 25 micron thick gold foil current collector is used.

In some embodiments, the electrochemical capacitor comprising one or more MOFs may have a relatively high capacitance retention percentage over a relatively large number of cycles. For instance, the electrochemical capacitor may have a capacitance retention percentage of at least about 75%, at least about 80%, at least about 85%, at least about 90%, at least about 92%, or at least about 95% after at least 1,000 cycles (e.g., 5,000 cycles, 10,000 cycles, 20,000 cycles) at constant current of 2 $A \cdot g^{-1}$ charge and discharge from 0 V to 2 V.

In some embodiments, the electrochemical capacitor comprising one or more MOFs may have a relatively low equivalent series resistance. For instance, the equivalent series resistance be less than or equal to about 3Ω, less than or equal to about 2Ω, less than or equal to about 1Ω, less than or equal to about 0.5Ω, or less than or equal to about 0.1Ω. In some instances, the equivalent series resistance may be between about 0.1Ω and about 3Ω, between about 0.1Ω and about 2Ω, between about 0.5Ω and about 1Ω, between about 0.1Ω and about 1Ω, or between about 0.1Ω and about 0.5Ω. One of ordinary skill in the art would be knowledgeable of methods to determine the equivalent series resistance. Briefly, the equivalent series resistance may be determined from the potential drop at the beginning of a constant current charge or discharge. The equivalent series resistance may be determined from the fitting electrochemical impedance data to the model equivalent circuit.

Definitions

For convenience, certain terms employed in the specification, examples, and appended claims are listed here.

As used herein, the term "reacting" refers to the forming of a bond between two or more components to produce a stable, isolable compound. For example, a first component and a second component may react to form one reaction product comprising the first component and the second component joined by a covalent bond. That is, the term "reacting" does not refer to the interaction of solvents, catalysts, bases, ligands, or other materials which may serve to promote the occurrence of the reaction with the component(s).

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, the term "alkyl" is given its ordinary meaning in the art and refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some cases, the alkyl group may be a lower alkyl group, i.e., an alkyl group having 1 to 10 carbon atoms (e.g., methyl, ethyl, propyl, butyl, pentyl, hexyl, heptyl, octyl, nonyl, or decyl). In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, t-butyl, cyclobutyl, hexyl, and cyclohexyl.

The term "alkylene" as used herein refers to a bivalent alkyl group. An "alkylene" group is a polymethylene group, i.e., —$(CH_2)_z$—, wherein z is a positive integer, e.g., from 1 to 20, from 1 to 10, from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described herein for a substituted aliphatic group.

Generally, the suffix "-ene" is used to describe a bivalent group. Thus, any of the terms defined herein can be modified with the suffix "-ene" to describe a bivalent version of that moiety. For example, a bivalent carbocycle is "carbocyclylene", a bivalent aryl ring is "arylene", a bivalent benzene ring is "phenylene", a bivalent heterocycle is "heterocyclylene", a bivalent heteroaryl ring is "heteroarylene", a bivalent alkyl chain is "alkylene", a bivalent alkenyl chain is "alkenylene", a bivalent alkynyl chain is "alkynylene", a bivalent heteroalkyl chain is "heteroalkylene", a bivalent heteroalkenyl chain is "heteroalkenylene", a bivalent heteroalkynyl chain is "heteroalkynylene", and so forth.

The terms "alkenyl" and "alkynyl" are given their ordinary meaning in the art and refer to unsaturated aliphatic groups analogous in length and possible substitution to the alkyls described above, but that contain at least one double or triple bond respectively.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, t-butyl, n-pentyl, sec-pentyl, isopentyl, t-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "cycloalkyl," as used herein, refers specifically to groups having three to ten, preferably three to seven carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or hetercyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl" is given its ordinary meaning in the art and refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, alkoxyalkyl, amino, thioester, poly(ethylene glycol), and alkyl-substituted amino.

The terms "heteroalkenyl" and "heteroalkynyl" are given their ordinary meaning in the art and refer to unsaturated aliphatic groups analogous in length and possible substitution to the heteroalkyls described above, but that contain at least one double or triple bond respectively.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CHF$_2$; —CH$_2$F; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "aryl" is given its ordinary meaning in the art and refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. Substituents include, but are not limited to, any of the previously mentioned substituents, i.e., the substituents recited for aliphatic moieties, or for other moieties as disclosed herein, resulting in the formation of a stable compound. In some cases, an aryl group is a stable mono- or polycyclic unsaturated moiety having preferably 3-14 carbon atoms, each of which may be substituted or unsubstituted. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups.

The terms "heteroaryl" is given its ordinary meaning in the art and refers to aryl groups comprising at least one heteroatom as a ring atom. A "heteroaryl" is a stable heterocyclic or polyheterocyclic unsaturated moiety having preferably 3-14 carbon atoms, each of which may be substituted or unsubstituted. Substituents include, but are not limited to, any of the previously mentioned substituents, i.e., the substitutes recited for aliphatic moieties, or for other moieties as disclosed herein, resulting in the formation of a stable compound. In some cases, a heteroaryl is a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will also be appreciated that aryl and heteroaryl moieties, as defined herein may be attached via an alkyl or heteroalkyl moiety and thus also include -(alkyl)aryl, -(heteroalkyl)aryl, -(heteroalkyl)heteroaryl, and -(heteroalkyl)heteroaryl moieties. Thus, as used herein, the phrases "aryl or heteroaryl moieties" and "aryl, heteroaryl, -(alkyl)aryl, -(heteroalkyl)aryl, -(heteroalkyl)heteroaryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$F; —CHF$_2$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

The terms "halo" and "halogen" as used herein refer to an atom selected from the group consisting of fluorine, chlorine, bromine, and iodine.

It will be appreciated that the above groups and/or compounds, as described herein, may be optionally substituted with any number of substituents or functional moieties. That is, any of the above groups may be optionally substituted. As used herein, the term "substituted" is contemplated to include all permissible substituents of organic compounds, "permissible" being in the context of the chemical rules of valence known to those of ordinary skill in the art. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

The following examples are intended to illustrate certain embodiments of the present invention, but do not exemplify the full scope of the invention.

EXAMPLES

Working Example 1

This example describes the preparation and use of two-dimensional (2D) electronic hybrid organic-inorganic materials (e.g., MOFs) that are connected through square-planar metal-bis(ortho-phenylenediimine) units (FIG. 1). These materials conduct electricity and may be used in the semiconductor, chemical, and electronics industries, including in applications such as electrochemical sensors, electrocatalysts, and various electronic devices such as light-emitting diodes, photovoltaic solar cells, and transistors. The MOFs are built from molecular precursors and comprise of organic ligands that contain at least two ortho-phenylenediimine units, and metal ions that connect the organic ligands by binding to the nitrogen atoms of the phenylenediimine moieties. The molecular building blocks may be changed by synthetic manipulations or by changing the metal precursor, therefore, the materials described in this example have variable (tunable) electrical conductivity and/or bandgap that are desirable for the applications listed above.

In FIG. 1: The metal (M)-bis(ortho-diimine) unit that connects the organic ligands in the materials described in this example. The squiggly bonds indicate connection to the extended material.

In the methods described in this example, MOFs are synthesized by the reaction of organic ligands containing at least two ortho-phenylenediamine groups with metal salts. During the course of the reaction, the organic ligands are oxidized and each ortho-phenylenediamine groups are transformed into ortho-phenylenediimine groups, which bind to the metal ion. Oxidation of the ortho-diamine groups and formation of the ortho-diimine groups aids in the electrical conductivity of the MOF. Oxidation may be achieved either with air ($O_2$), or with chemical oxidants, such as ferricinium, $[Fe(C_5H_5)]^+$, or other oxidizers. A base, such as ammonia (or ammonium hydroxide) may be utilized to deprotonate the diamine and to form the ortho-diimine groups in the 2D material.

Synthesis of $Ni_3(HITP)_2$
(HITP=2,3,6,7,10,11-hexaiiminotriphenylene)

(FIG. 2) Reaction between $NiCl_2 \cdot 6H_2O$ (6.6 mg, 0.028 mmol) in 5 mL of water and 0.3 mL of concentrated aqueous ammonia ($NH_4OH$, 14 mol·$L^{-1}$) and 2,3,6,7,10,11-hexaaminotriphenylene hexahydrochloride (HATP, 10 mg, 0.019 mmol) in 5 mL of water produced a black powder and blue-violet films of $Ni_3(HITP)_2$ after stirring at 65° C. for 2 hours under open air in a beaker. The resulting black powder was centrifuged and washed with water, followed by extensive washing (for 1 hour) with water in an ultrasonic bath.

Figure 2:
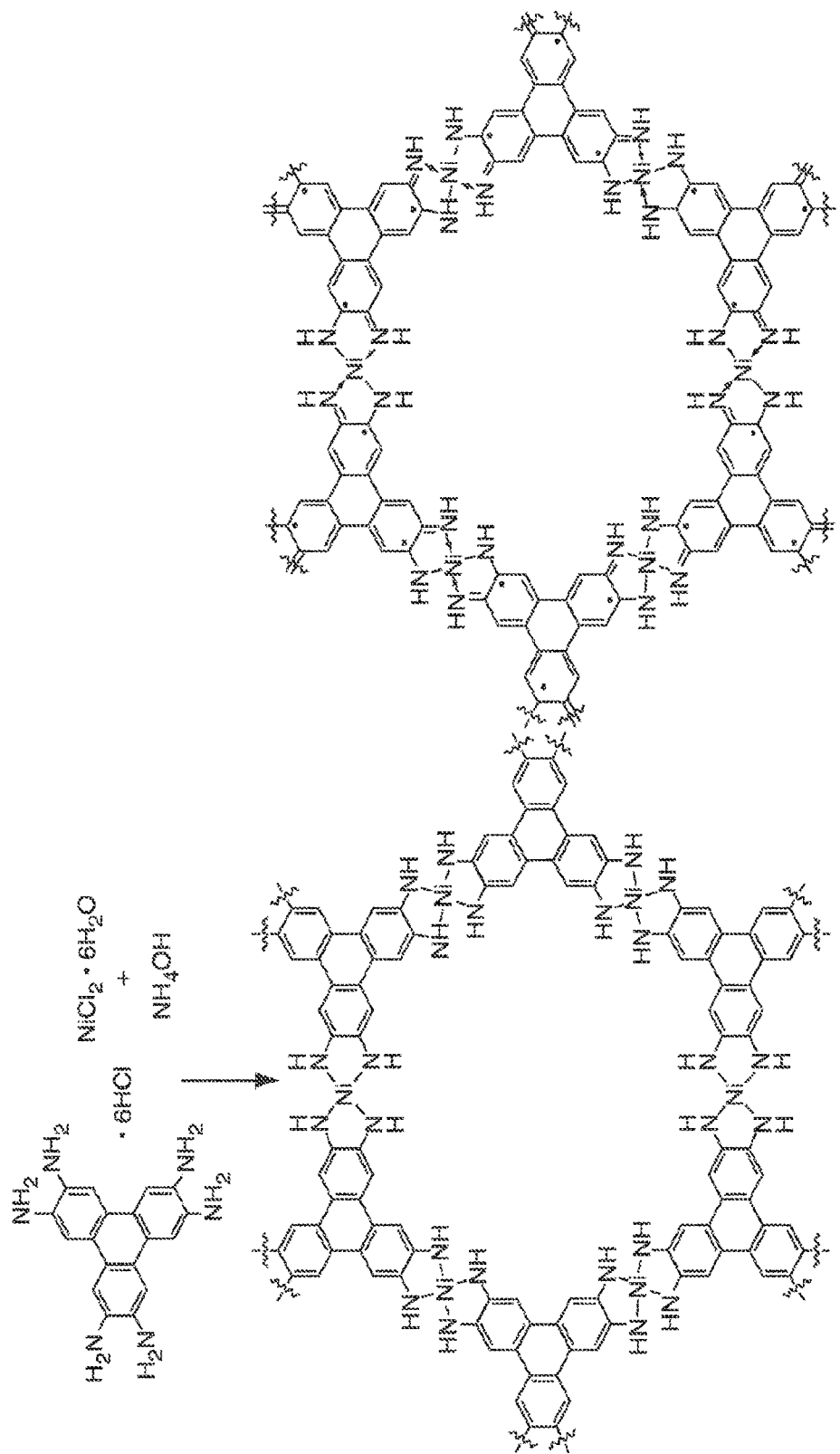
FIG. 2 illustrates a synthetic method for a non-limiting MOF, according to some embodiments.

In FIG. 2: Synthesis of $Ni_3(HITP)_2$, a representative example for the materials described herein. A second resonance form of $Ni_3(HITP)_2$, displaying the di-radical nature of the bis-diamine linkages is also shown on the right. Dark blue films of $Ni_3(HITP)_2$ were obtained on quartz, glass, indium-tin oxide coated glass, and silicon wafers, among others.

Thermogravimetric analysis of $Ni_3(HITP)_2$ (FIG. 3) showed that the material lost some guest water molecules and was be dried by heating at temperature between 100 and 300° C. Thermal decomposition occurred above ~300° C.

Figure 3:
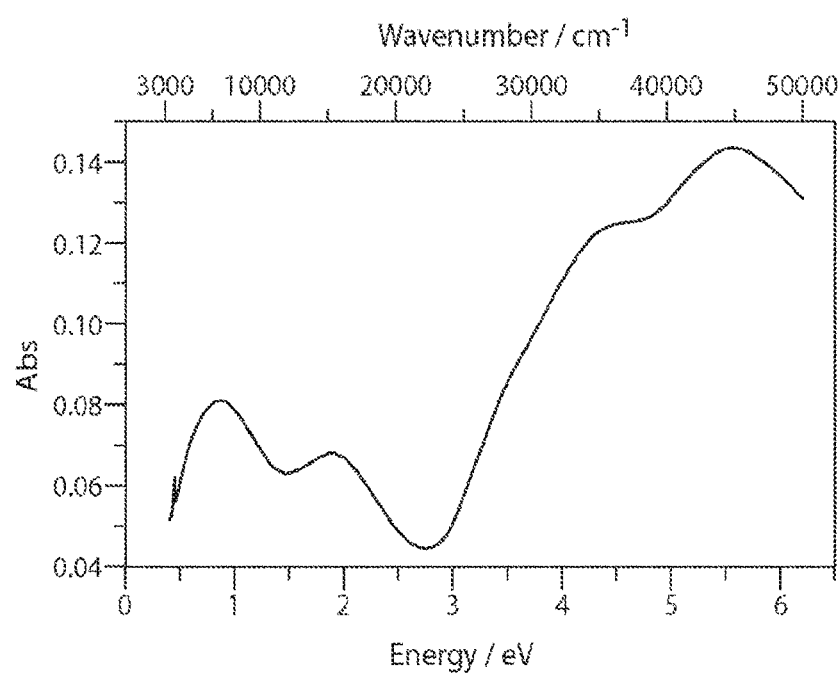
FIG. 3 shows UV-Vis-NIR absorption spectra for non-limiting MOFs, according to some embodiments.

A UV-vis spectrum of $Ni_3(HITP)_2$ (FIG. 3) showed electronic transitions in the near-IR, indicative of extended conjugation, as is common for organic conducting polymers. In FIG. 3: UV-Vis-NIR absorption of a $Ni_3(HITP)_2$ film on quartz slide.

X-ray photoelectron spectra (XPS) of $Ni_3(HITP)_2$ showed that a single type of Ni atoms and a single type of N atoms were present in the sample, evidencing that $Ni_3(HITP)_2$ was neutral, not charged and that no additional cations, anions, or metallic species (e.g. Ni metal) were present in the sample other than the Ni and N atoms pertaining to the Ni-bis(ortho-phenylenediimine) units and the organic ligands.

Figure 4:
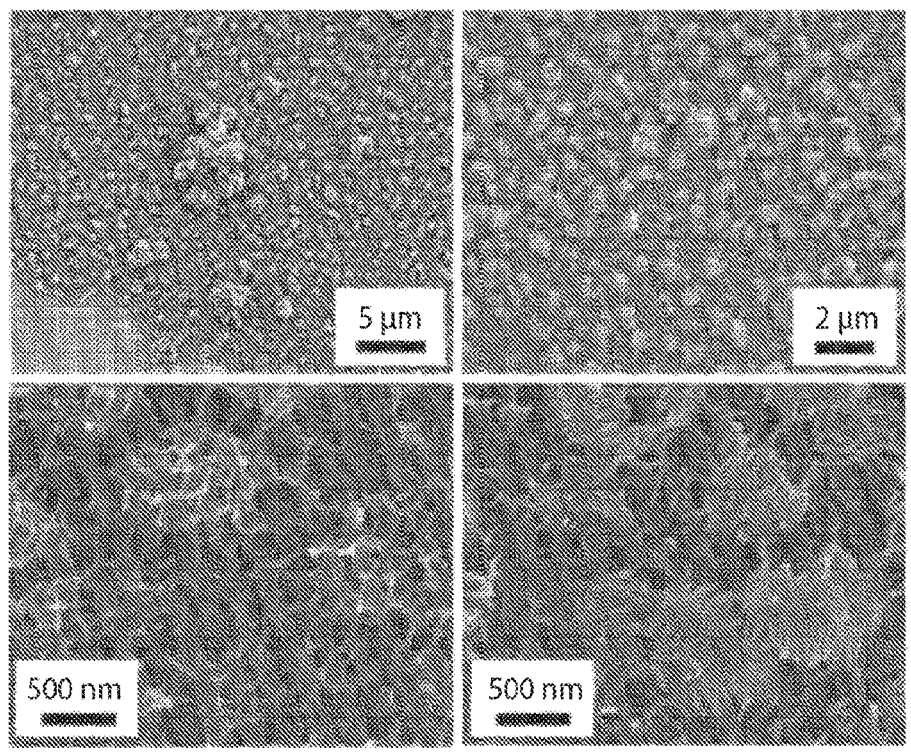
FIG. 4 shows SEMs (top) and AFM images (bottom) for non-limiting MOFs, according to some embodiments.
Figure 4:
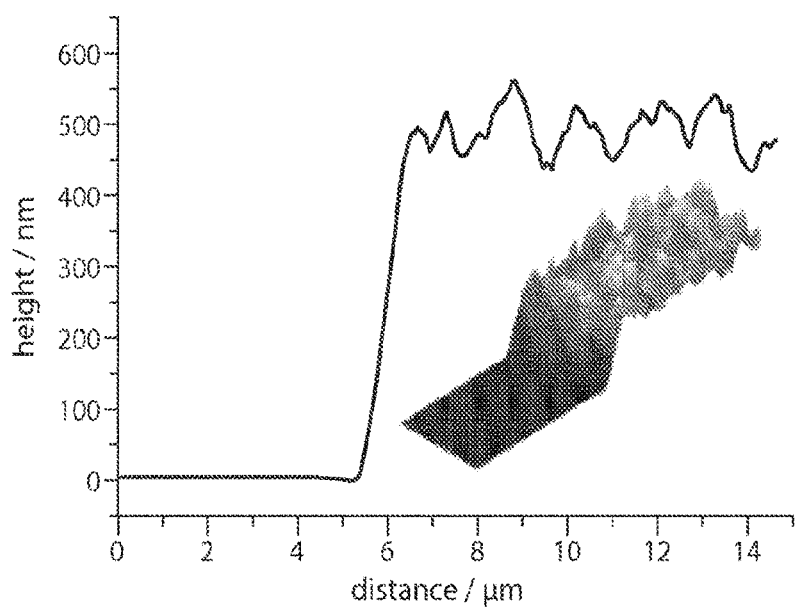

Films of $Ni_3(HITP)_2$ were grown on quartz and other surfaces. Scanning electron micrographs (SEMs) and atomic force microscopy (AFM) images of representative films grown on quartz are shown in FIG. 4. In FIG. 4: SEMs for films of $Ni_3(HITP)_2$ at various magnifications (top). AFM thickness profile and corresponding 3D AFM image of a representative $Ni_3(HITP)_2$ film (bottom).

Figure 5:
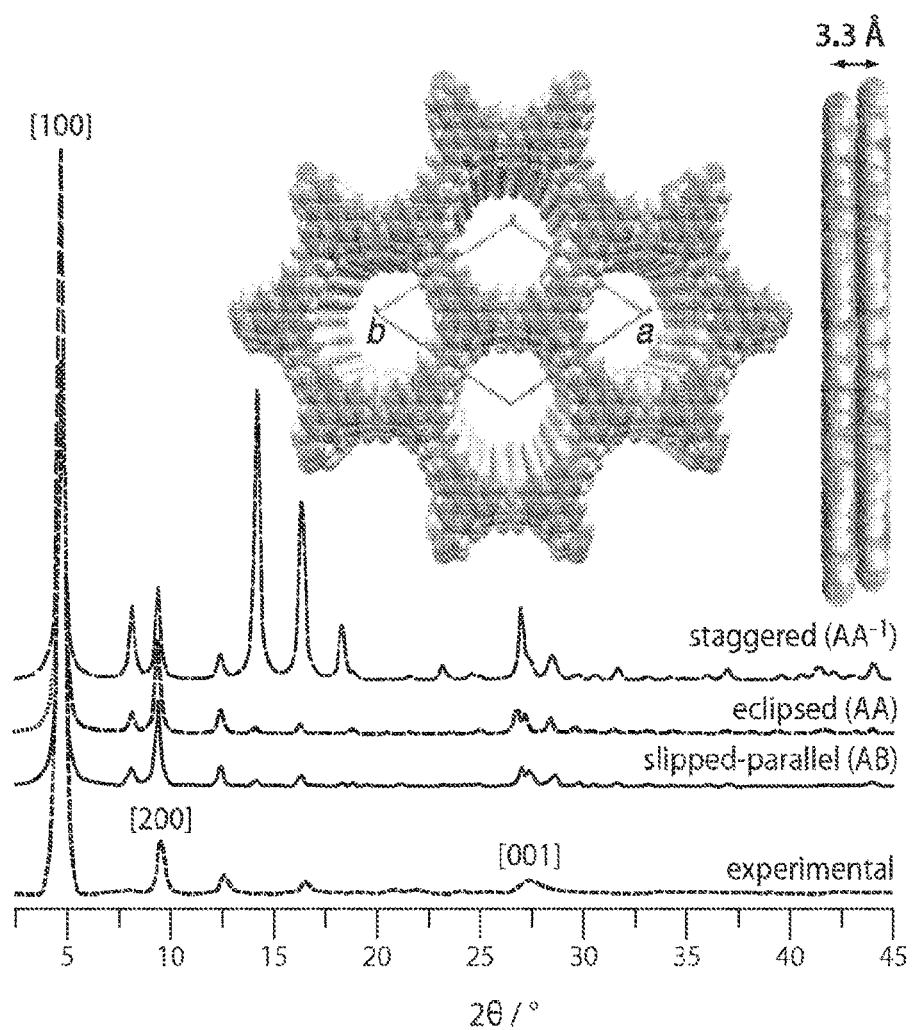
FIG. 5 shows experimental and simulated PXRD spectra for a non-limiting MOF, according to some embodiments.

$Ni_3(HITP)_2$ exhibited a sheet (layered) structure, where conjugation occurs in the plane, and sheets were arranged in a shifted-parallel alignment, as shown in FIG. 5. FIG. 5 also shows powder X-ray diffraction data where experimental results matched the proposed layered structure. In FIG. 5: Experimental and simulated PXRD patterns of $Ni_3(HITP)_2$. The inset shows the slipped-parallel structure with neighboring sheets displaced by 1/16 fractional coordinates in the a and b directions.

The electrical conductivity of $Ni_3(HITP)_2$ was measured in polycrystalline pellet form and in polycrystalline film form. A pellet of this material compressed between two steel rods and subjected to a two-probe direct current measurement revealed a conductivity of 2 S·cm$^{-1}$. A van der Pauw conductivity measurement measured for a 500 nm thick film of $Ni_3(HITP)_2$ deposited on a quartz substrate revealed a conductivity of 40 S·cm$^{-1}$. The film conductivity had a linear dependence with temperature.

Prophetic Example 1

The approach of using metal bis(ortho-phenylenediimine) units for the construction of electrically conducting hybrid organic-inorganic materials as described in working Example 1 may be modified to include, for example:

a) The use of any aromatic organic molecule that contains at least two ortho-diamine units that may be arranged in any geometry around the organic core. The diamine unit, in contact with an oxidant, a base, and with a metal ion may produce the metal bis(ortho-diimine) unit. Non-limiting organic ligands include ligands with linear geometry (e.g., 2,3,6,7-tetraaminonaphthalene, 1,2,4,5-tetraaminobenzene), trigonal geometry (e.g., HATP and extensions thereof with fused benzene rings that may or might not contain heteroatoms such as N), and square geometry (e.g., octaaminophthalocyanine, and its linearly extended congeners with additional fused benzene rings that may or might not contain heteroatoms such as N);

b) The use of other organic ligands that contain at least two ortho-diamine units and any combination of benzene rings and heterocyclic rings as the ligand core (e.g., thiophene, carbazole, pyrole, indole, furan);

c) The use of organic ligands including other functional groups that generally do not bind a metal (e.g., —$NO_2$, —R; R=alkyl; —Ar; Ar=aryl, —F, —Br, —I, —CN, —$SO_3H$, —OH, —SH, —NC, —$PO_3H$, —$CF_3$, —$NH_2$). These functional groups may be used to modulate the electronic properties of the ligand, and therefore the electrical properties of the ensuing MOFs;

d) The use of other divalent metal ions including, but not limited to, $Mg^{2+}$, $Mn^{2+}$, $Fe^{2+}$, $Co^{2+}$, $Ni^{2+}$, $Cu^{2+}$, $Pd^{2+}$, $Pt^{2+}$, $Ru^{2+}$, $Cd^{2+}$, $Zn^{2+}$, $Pb^{2+}$, $Hg^{2+}$, $V^{2+}$, and $Cr^{2+}$;

e) The use monovalent ions including, but not limited to, $Ag^+$, $Cu^+$, and $Au^+$;

f) The use of trivalent ions including, but not limited to, $Fe^{3+}$, $V^{3+}$, $Ti^{3+}$, $Sc^{3+}$, $Al^{3+}$, $In^{3+}$, $Ga^{3+}$, $Mn^{3+}$, $Co^{3+}$, and $Cr^{3+}$;

g) The use of any salts of the metal cations in the synthesis (e.g., $F^-$, $Br^-$, $I^-$, $NO_3^-$, $SO_4^{2-}$, $ClO_4^-$, other oxoanions);

h) The use of any oxidants that may substitute air or $O_2$ (e.g., ferricinium, nitrosonium, $Ag^{2+}$, $Ag^+$, other chemical oxidants); and/or i) The use of any bases that may substitute $NH_3$ (e.g., $NH_4OH$).

Working Example 2

The following example provides additional details regarding the materials and synthesize of the MOFs prepared in Working Example 1.

Materials:

Starting materials were purchased from Sigma-Aldrich or TCI and used without further purification. Tris(Dibenzylideneacetone)dipalladium(0), $Pd_2(dba)_3$, was purchased from Oakwood Products, Inc. (Fluorochem Ltd.). 2,3,6,7,10,11-hexaaminotriphenylene hexahydrochloride, HATP.6HCl, was prepared according to known procedures. Hexane, diethyl ether, ethyl acetate, toluene and silica-gel were purchased from VWR. THF was collected from an alumina column solvent purification system.

Exemplary Synthesis of $Ni_3(HITP)_2$:

A solution of 6.6 mg (0.028 mmol) of nickel chloride hexahydrate ($NiCl_2.6H_2O$) in 5 mL of water and 0.3 mL of concentrated aqueous ammonia ($NH_4OH$, 14 mol·L$^{-1}$) was added to a solution of 10 mg (0.019 mmol) of HAPT.6HCl in 5 mL of water. This mixture was stirred in an open beaker for 2 hours at 65° C. The resulting black powder was centrifuged and washed with water, followed by extensive washing (for 1 hour) with water in an ultrasonic bath and additional washing by boiling in water for 24 hours. The solid was then dried under vacuum at 150° C. C, H, N, and Cl microelemental analysis for $Ni_3(C_{18}H_{12}N_6)_2$: Calculated: C: 54.00%; H: 3.02%; N: 20.99%; Cl: 0.00%. Found: C: 53.84%; H: 3.12%; N: 20.83%; Cl: <0.02%. A dark blue film was obtained by placing a quartz substrate on a Teflon holder such that it was positioned upside-down inside the reaction vessel. The film growth was thus independent of compacting due to gravity.

Methods:

Absorption spectra were taken with a CARY 5000 UV-Vis-NIR spectrophotometer.

Thermogravimetric analysis (TGA) was performed on a TA Instruments Q500 Thermogravimetric Analyzer at a heating rate of 0.5° C./min under a nitrogen gas flow of 90 mL/min on a platinum pan.

Powder X-ray diffraction (PXRD) patterns were recorded with a Bruker D8 Advance diffractometer equipped with a Göbel mirror, rotating sample stage, LynxEye detector and Cu K$_\alpha$ ($\lambda$=1.5405 Å) X-ray source in a θ/2θ Bragg-Brentano geometry. Anti-scattering incident source slit (typically 1 mm) and an exchangeable steckblende detector slit (typically 8 mm) were used. The tube voltage and current were 40 kV and 40 mA, respectively. Knife-edge attachments were used to remove scattering at low angles. Samples for PXRD were prepared by placing a thin layer of the designated materials on a zero-background silicon (510) crystal plate.

Scanning electron microscopy (SEM) images were recorded using a Leo Supra 55VP FEG SEM with an operating voltage of 3 keV.

X-ray photoelectron spectroscopy (XPS) was performed on a Thermo Scientific K-Alpha system equipped with an Al source and 180° double focusing hemispherical analyzer and 128-channel detector using a 400 μm X-ray spot size.

AFM topography images were acquired using an Asylum MFP-3D AFM system. Images were recorded in tapping mode in the air at room temperature (20-23° C.) using silicon micro cantilevers (OMCL-AC200TS-*3, Olympus). The set point ratio was adjusted to 0.75-0.8 (corresponding to "light" tapping) and the scan rate was set to 0.5 Hz. Imaging was carried out in different scan directions and at different scales to verify the consistency and robustness of the evaluated structures. The thickness of films was measured by AFM profilometry.

Conductivity measurements on films were performed using the van der Pauw method under temperature control with a 4-arm Lakeshore probe station under vacuum (ca.

$10^{-5}$ torr). Electrical measurement data were obtained using a Keithley 2400 source/meter by manually changing the probe connections. Four silver or carbon paste contacts were put on the corners of 3×3 mm$^2$-8×8 mm$^2$ squares of uniform film separated from the rest of the sample.

Powder conductivity were measured using a home-built press as has been described elsewhere.[2] The powder was pressed between two steel rods of 2 mm diameter inside of a glass capillary. The thickness of the powder pellets ranged from 0.1 mm to 0.5 mm.

X-ray absorption measurements were conducted on the Materials Research Collaborative Access Team (MR-CAT) beam lines at the Advanced Photon Source of Argonne National Laboratory. The Ni K edge (8333 eV) was measured on a bending magnet beam line and a spectrum of the elemental foil was collected alongside sample measurements to calibrate the energy. A water-cooled, double-crystal Si(111) monochromator was used to select the photon energies and the experiments were performed in transmission mode with argon, helium, and N$_2$-filled ionization chambers. Data was collected in six regions (energies relative to the elemental Ni K edge): a pre-edge region 250 to 30 eV (10 eV step size, dwell time 0.5 s), initial XANES region −30 to −12 eV (5 eV step size, dwell time −0.5 s), XANES region −12 to 30 eV (1 eV step size, dwell time 1 s), an initial EXAFS region −30 eV to 6 k (0.05 k step size, dwell time 2 s), middle EXAFS region 6 k to 12 k (0.05 k step size, dwell time 4 s), and a final EXAFS region 12 k to 15 k (0.05 k step size, dwell time 8 s). The sample was prepared in an argon glove box and diluted with sufficient boron nitride to acquire an appropriate step height in the spectrum. This mixture was loaded into a 4 mm diameter cylindrical sample holder and kept under argon in a quartz tube capped with Kapton tape during the measurement. The edge energy was associated with the maximum of the first derivative of the XANES spectrum. Athena 0.8.061 was used to normalize and calibrate the data and Artemis 0.8.014 to simulate spectra of model structures determined by density functional theory. These simulations represent the sums of all calculated scattering paths.

Working Example 3

In recent years there has been steadily increasing interest in using metal-organic frameworks (MOFs) as next-generation functional materials in electronic and optoelectronic devices. Due to a combination of high surface area and robust chemical tunability based on a "bottom-up" synthetic approach, MOFs have been targeted for use in sensors. An ongoing challenge, however, has been a lack of efficient signal transduction due to the fact that the vast majority of MOFs are insulators. Accordingly, the utility of metal-organic frameworks (MOFs) as functional materials in electronic devices has been limited to date by a lack of MOFs that display high electrical conductivity. MOFs with high intrinsic charge mobility or electrical conductivity would provide an opportunity for the development of MOF-based devices. This example, describes the synthesis of a new electrically conductive 2D MOF, $Cu_3(HITP)_2$ (HITP=2,3,6,7,10,11-hexaiminotriphenylene), which displayed a bulk conductivity of 0.2 S·cm$^{-1}$ (pellet, two-probe). Devices synthesized by simple drop casting of neat $Cu_3(HITP)_2$ functioned as reversible chemiresistive sensors, capable of detecting sub-ppm levels of ammonia vapor. Comparison with the isostructural 2D MOF $Ni_3(HITP)_2$ revealed that the copper sites were critical for ammonia sensing, indicating that rational synthesis could be used to tune the functional properties of conductive MOFs.

2D MOFs have the high conductivity values, likely due to in-plane charge delocalization and extended π-conjugation in the 2D sheets, mediated by electronic communication through the metal nodes. As described in Working Example 1, the 2D MOF $Ni_3(HITP)_2$ (HITP=2,3,6,7,10,11-hexaiminotriphenylene) displayed a very high conductivity compared to other microporous MOF reported to date. These results indicated that 2D MOFs with o-phenylenediamine linkages were attractive materials candidates along with structurally related 2D MOFs with dithiolene or o-semiquinone linkages. Therefore, a family of MOFs based on the $Ni_3(HITP)_2$ framework was investigated in order to probe the effect of structural changes on resulting electronic properties. It was hypothesized that through systematic variation of the metal center, the overall electronic structure of the 2D sheets may be tuned, leading to diverse properties and functionality. In this example, the replacement of the Ni sites in $Ni_3(HITP)_2$ with Cu which resulted in an isostructural 2D MOF that maintained high electrical conductivity. The choice of metal had a dramatic effect on the response of conductivity to analytes such as ammonia vapor, highlighting the potential for rational synthetic tuning of conductive MOFs to afford desirable properties.

Synthesis of $Cu_3(HITP)_2$.

Figure 6:
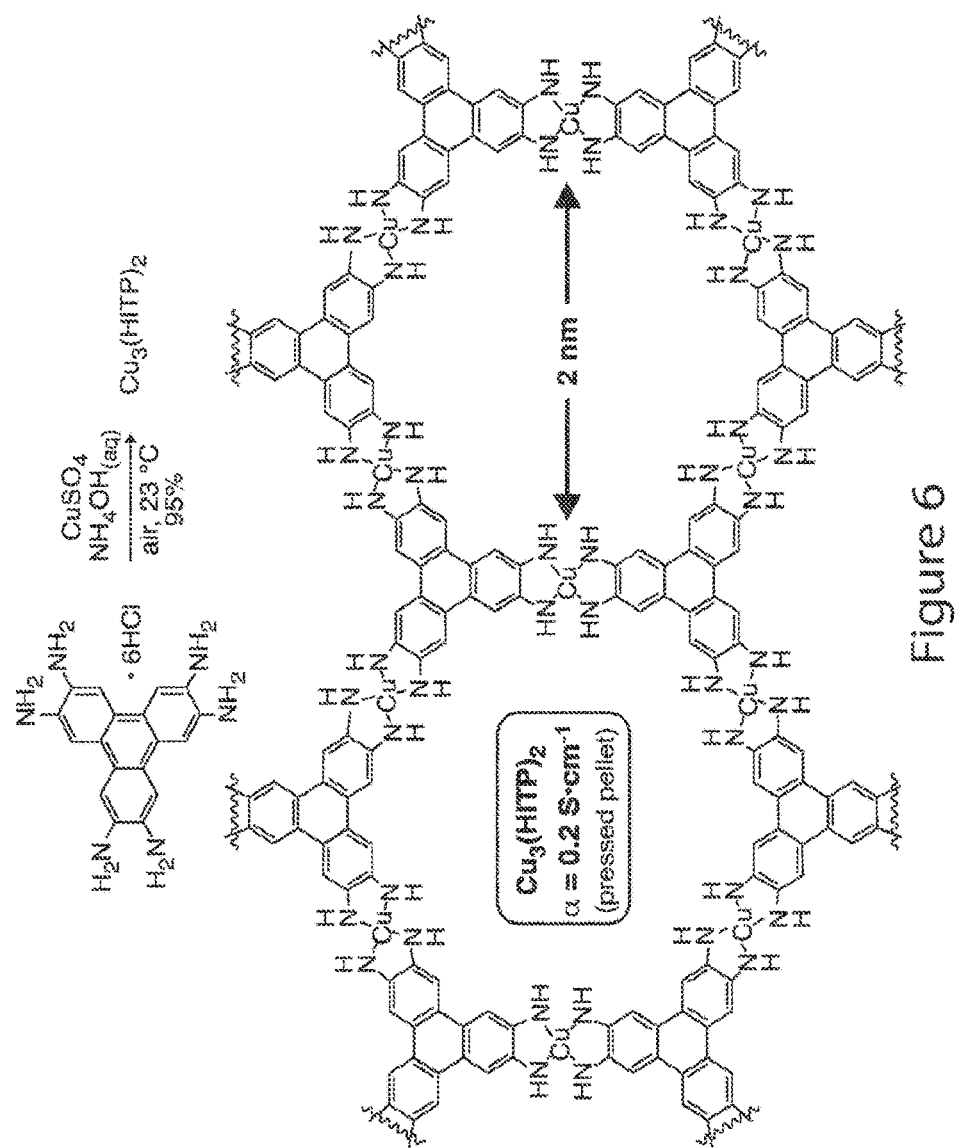
FIG. 6 illustrates a synthetic method for a non-limiting MOF, according to some embodiments.
Figure 7:
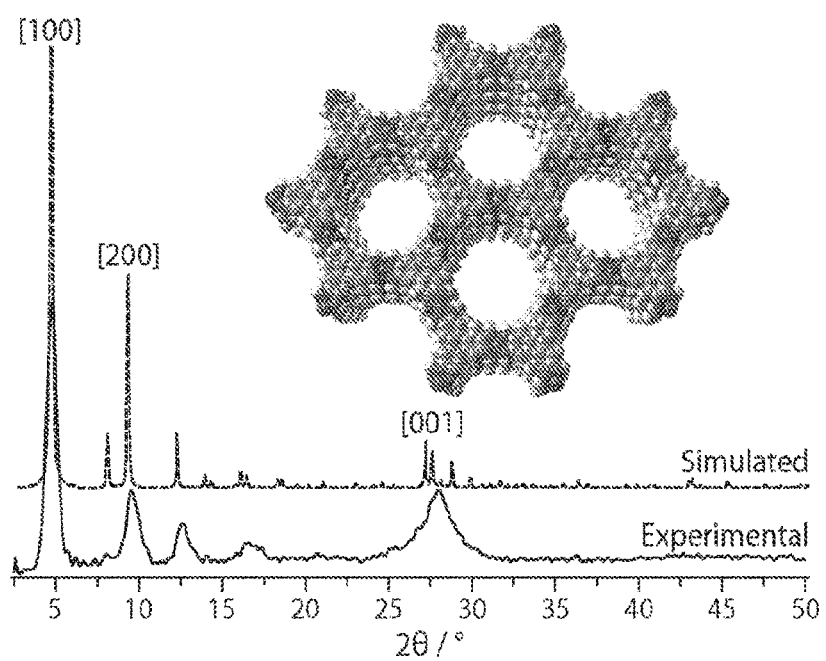
FIG. 7 shows experimental and simulated PXRD spectra for a non-limiting MOF, according to some embodiments.

Synthesis of $Cu_3(HITP)_2$ was accomplished using similar conditions as for $Ni_3(HITP)_2$: a solution of $CuSO_4$ in dilute aqueous ammonia was combined with 2,3,6,7,10,11-hexaaminotriphenylene hexahydrochloride (HATP.6HCl) under air at 23° C., resulting in rapid precipitation of a black solid. After washing with water and acetone, followed by drying under vacuum, $Cu_3(HITP)_2$ was isolated as a black crystalline solid in 95% yield. The synthesis and 2D chemical structure of $Cu_3(HITP)_2$ is shown in FIG. 6. Powder X-ray diffraction (PXRD) analysis, shown in FIG. 7, revealed that $Cu_3(HITP)_2$ was isostructural with $Ni_3(HITP)_2$, and adopted a hexagonal 2D structure with a slipped-parallel stacking of the 2D sheets. FIG. 7 shows experimental and simulated PXRD patterns for $Cu_3(HITP)_2$, displaying a slipped-parallel packing structure of the 2D sheets. The inset shows a structure of $Cu_3(HITP)_2$ viewed down the c axis. The unit cell parameters for the simulated structure were a=b=22.3 Å and c=6.6 Å. The broadness of the peak at 2θ=27.8°, corresponding to the [001] reflections, suggested poorer long-rage order along the c direction as compared to the ab plane, which was typical for layered 2D materials. Conductivity of the bulk material was assessed by two-probe measurement of a pressed pellet, and a room temperature conductivity of 0.2 S·cm$^{-1}$ was obtained. This value was slightly lower than measured for $Ni_3(HITP)_2$ (2 S·cm$^{-1}$), but was higher than for the majority of conductive MOFs reported to date, including 2D MOFs with dithiolene or o-semiquinone linkages.

X-ray photoelectron spectroscopy (XPS) analysis established that $Cu_3(HITP)_2$ was a charge-neutral material, as previously observed for $Ni_3(HITP)_2$. After washing with water, no residual $SO_4^{2-}$ or $Cl^-$ anions were detected by XPS, and high-resolution scans of the N(1s) region showed a single type of N atom, confirming that additional $NH_4^+$ cations were also not present. While the chemical structure of $Cu_3(HITP)_2$ shown in FIG. 6 was drawn in a closed-shell configuration for simplicity, each of the o-phenylenediamine linkages was expected to be oxidized to a radical anion form, which resulted in a charge-neutral complex with the $Cu^{2+}$ centers. Interestingly, a high-resolution XPS spectrum of the Cu(2p) region suggested an inherent mixed-valency of the Cu centers in $Cu_3(HITP)_2$, which contrasts with $Ni_3(HITP)_2$, for which a single type of Ni atom was observed. The lack of charge balancing counterions indicated that any variation from $Cu^{2+}$ was compensated by the redox-active HITP ligands; hexaaminotriphenylene derivatives are well known to accommodate a wide range of redox states. While Cu metal formation has been reported as a potential side reaction in the synthesis of complexes of $Cu^{2+}$ with o-phenylenediamine, control experiments showed that Cu metal was not formed in the synthesis of $Cu_3(HITP)_2$.

Figure 8:
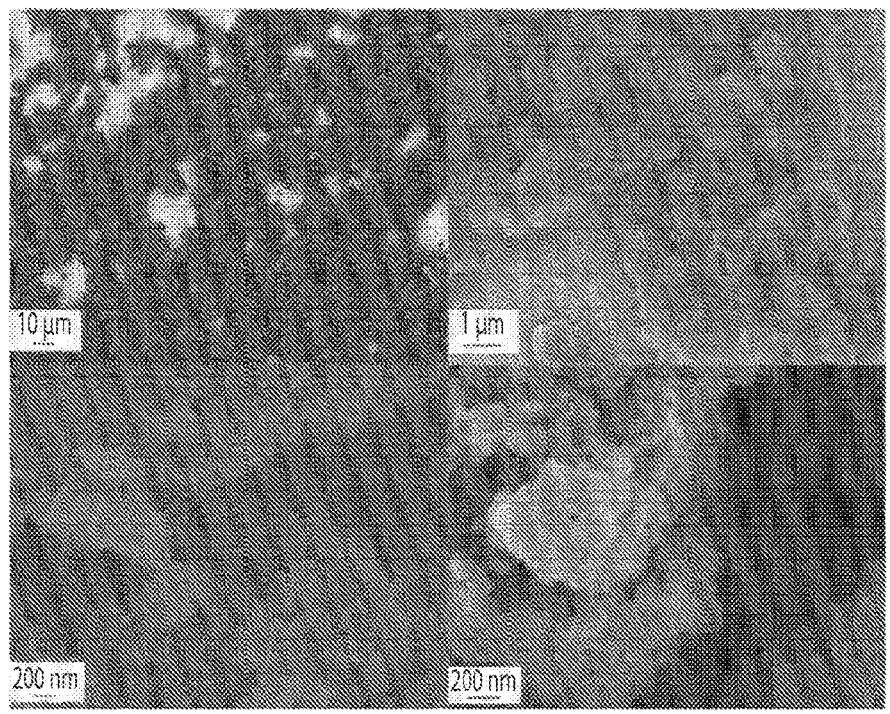
FIG. 8 shows SEMs images for non-limiting MOFs, according to some embodiments.

Scanning electron microscopy (SEM) was used to probe the morphology of bulk $Cu_3(HITP)_2$, and revealed submicron sized crystallites that pack together to form a denser polycrystalline material. Films obtained by drop-casting a suspension of $Cu_3(HITP)_2$ in acetone onto substrates such as ITO glass were mechanically robust, and did not separate from the substrate upon vigorous washing in an ultrasonic bath. FIG. 8 shows SEM images at various magnifications for $Cu_3(HITP)_2$, drop-cast onto an ITO glass slide from a suspension in acetone. The ability to process films of conductive MOFs by simple methods such as drop casting is potentially valuable for device manufacturing, as demonstrated in this example for the fabrication of chemiresistive sensors with $Cu_3(HITP)_2$.

Reversible Chemiresistive Sensing.

Figure 9:
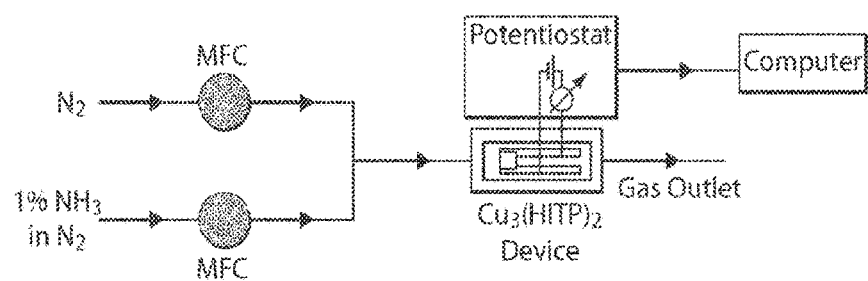
FIG. 9 illustrates a schematic of an apparatus used in chemiresistive sensing, according to some embodiments.
Figure 10:
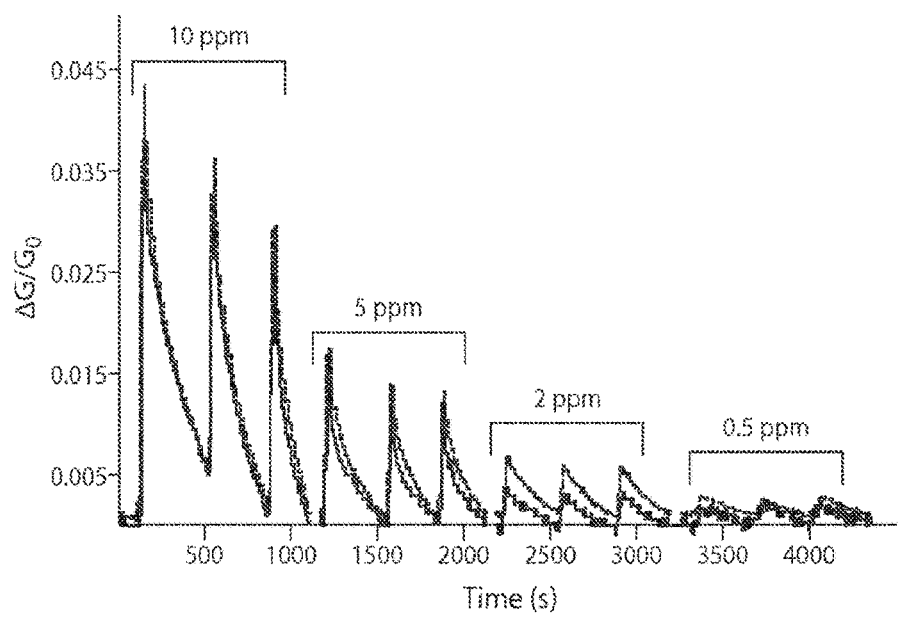
FIG. 10 shows a graph of the relative response of a non-limiting MOF device to various concentrations of ammonia diluted with nitrogen gas, according to some embodiments.
Figure 11:
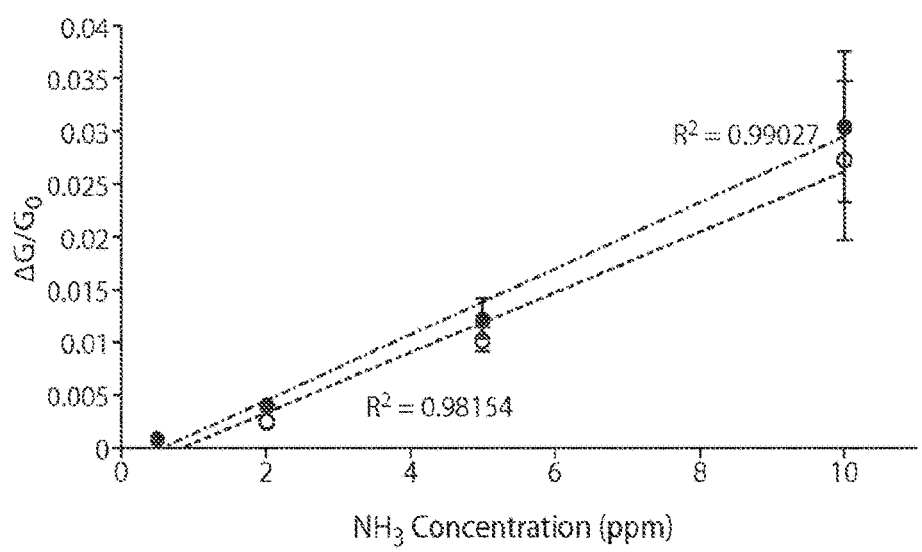
FIG. 11 shows a graph of the response of a MOF device versus ammonia concentration, according to some embodiments.

A reversible chemiresistive sensor of ammonia vapor was formed by drop-casting an acetone suspension of $Cu_3(HITP)_2$ onto interdigitated gold electrodes. The $Cu_3(HITP)_2$ device was encased in a Teflon gas flow chamber, with its electrodes connected to a potentiostat. During a measurement the device was held at a constant applied potential of 100 mV, and the current was monitored while a continuous gas stream was passed over the device at a constant flow rate, which could be switched between $N_2$ and an ammonia/$N_2$ mixture. A stable baseline current was established under $N_2$ flow, and then a sharp increase in current was observed within seconds upon exposure to dilute ammonia vapor. A schematic of the experimental apparatus used for ammonia sensing is shown in FIG. 9. FIG. 10 is a graph of the relative response of a $Cu_3(HITP)_2$ device to 0.5 ppm, 2 ppm, 5 ppm, and 10 ppm ammonia diluted with nitrogen gas (data from two separate devices is overlaid). The starting current level was recovered when the ammonia flow was replaced with pure $N_2$, and the reversible change in current was observed over >10 cycles. Ammonia concentrations of ≤0.5 ppm were detected even after exposure to higher concentrations. A concentration of 0.5 ppm was the lowest experimentally accessible concentration of ammonia for our apparatus. The observed sensitivity toward ammonia vapor was competitive with values reported for chemiresistive sensors based on pristine carbon nanotubes (CNTs) and conductive polymers such as PEDOT, as well as reported chemical sensors based on transistors fabricated from monolayer 2D crystals of $MoS_2$ grown by chemical vapor deposition (CVD). Furthermore, detection of sub-ppm levels of ammonia was sufficient for air quality monitoring according to EPA guidelines, as well as for typical agriculture and livestock applications. Within the measured range of ammonia concentrations, the change in relative response was linear, indicating that devices fabricated from $Cu_3(HITP)_2$ could be used for quantitative sensing. FIG. 11 is a graph of the response of $Cu_3(HITP)_2$ devices versus ammonia concentration (data from two separate devices is overlaid). The "turn-on" response to ammonia vapor observed for $Cu_3(HITP)_2$ devices was also of interest. In many reported chemiresistive sensors, such as those based on CNTs and conductive polymers, ammonia exposure results in decreased conductance due to hole quenching. Sensors based on metal chalcogenides, on the other hand, typically exhibit a turn-on response similar to $Cu_3(HITP)_2$. The data therefore indicates that $Cu_3(HITP)_2$ was likely not a hole conductor, and may find complimentary uses to existing CNT and polymer sensor materials.

In contrast to the results obtained for $Cu_3(HITP)_2$, devices fabricated from $Ni_3(HITP)_2$ did not display any observable response to ammonia vapor exposure under identical experimental conditions. These results indicated that rational synthetic variation of conductive MOFs could have a direct impact on functionality such as chemiresistive sensing. Recent theoretical studies have described how the identity of the metal center is expected to impact the electronic properties of $M_3(HITP)_2$ materials (M=transition metal). For example, replacement of Ni with metals of higher d-electron count, such as Cu, was predicted to significantly increase the energy of the Fermi level as compared to $Ni_3(HITP)_2$. Such changes in electronic structure were likely related to observed differences in chemiresistive response, and point to a potential strategy for tuning the selectivity of the material towards different types of analytes.

In conclusion, the synthesis of $Cu_3(HITP)_2$, a new 2D MOF with high electrical conductivity has been described. The results demonstrated that targeting 2D frameworks based on o-phenylenediamine linkages was a general strategy for the synthesis of conductive MOFs. It was established that such materials can be used for the fabrication of simple chemiresistive sensor devices, and that the response of isostructural MOFs can be tuned by choice of metal center. These results suggest a promising approach toward the targeted synthesis of new sensing materials based on rational synthetic variation of conductive MOFs.

Working Example 4

The following example provides additional details regarding the materials and synthesis of the MOF prepared in Working Example 3.

Materials.

Commercially available chemicals were purchased from Sigma-Aldrich or TCI, except for Tris(Dibenzylideneacetone)dipalladium(0) which was purchased from Oakwood Products. All reagents were used as received unless otherwise noted. 2,3,6,7,10,11-hexaaminotriphenylene hexahydrochloride (HATP.6HCl) was prepared according to a literature procedure (Chen, L.; Kim, J.; Ishizuka, T.; Honsho, Y.; Saeki, A.; Seki, S.; Ihee, H.; Jiang, D. J. Am. Chem. Soc. 2009, 131, 7287). Solvents were used as received without further purification.

Instrumentation.

Powder X-ray diffraction (PXRD) patterns were recorded with a Bruker D8 Advance diffractometer equipped with a Göbel mirror, rotating sample stage, LynxEye detector and Cu $K_\alpha$ (λ=1.5405 Å) X-ray source in a θ/2θ Bragg-Brentano geometry. An anti-scattering incident source slit (typically 1 mm) and an exchangeable steckblende detector slit (typically 8 mm) were used. The tube voltage and current were 40 kV and 40 mA, respectively. Knife-edge attachments were used to remove scattering at low angles. Samples for PXRD were prepared by placing a thin layer of the designated materials on a zero-background silicon (510) crystal plate.

Scanning electron microscopy (SEM) images were recorded using a Zeiss Ultra55 SEM equipped with an EDS detector, with an operating voltage of 5 keV. X-ray photoelectron spectroscopy (XPS) was performed on a Thermo Scientific K-Alpha system equipped with an Al source and 180° double focusing hemispherical analyzer and 128-channel detector using a 200 µm X-ray spot size.

Pressed-pellet conductivity was measured using a home-built press as previously described in the literature. The powder was pressed between two steel rods of 2 mm diameter inside of a glass capillary. The thickness of the powder pellets typically ranged from 0.1 mm to 0.5 mm.

Synthesis of $Cu_3(HITP)_2$.

Under air, a solution of HATP.6HCl (10. mg, $1.9 \times 10^{-2}$ mmol, 1.0 equiv) in distilled water (3 mL) was added all at once to a standing solution of $CuSO_4 \cdot 5H_2O$ (7.0 mg, $2.8 \times 10^{-2}$ mmol, 1.5 equiv) in distilled water (2 mL) and concentrated aqueous ammonia (14 M; 100 µL) at 23° C. Immediate precipitation of dark solids was observed, and the reaction mixture was allowed to stand for 3 hours. The mixture was then centrifuged and the supernatant decanted. The solids were vigorously stirred with distilled water (15 mL) at 23° C. for three days, and the water exchanged twice daily. Finally, the solids were stirred with acetone (15 mL) at 23° C. for one day, isolated by centrifugation, and then dried under vacuum (≤20 mTorr) at 23° C., affording $Cu_3(HITP)_2$ as a black solid (7.2 mg, 95% yield).

Procedure for $NH_3$ Sensing Measurements.

A suspension of freshly prepared $Cu_3(HITP)_2$ in acetone (~1 mg/mL) was drop cast onto interdigitated gold electrodes. The amount of material deposited was monitored by the device resistance, and starting values of 10-100 kΩ were targeted. The electrodes of the device were connected to a potentiostat and the device was enclosed in a custom built PTFE chamber. A gas mixer system, comprised of two digital mass flow controllers (MFCs), was used to deliver up to 2 mL/min of a mixture of 1% ammonia in nitrogen that was further diluted in the gas mixer with pure nitrogen delivered by the other MFC at 2.00 L/min. The potentiostat was used to apply a constant potential of 0.100 V across the electrodes, and the current was recorded as the device was exposed to various concentrations of ammonia for 30 s at a time with at least 300 s of pure nitrogen flow between successive measurements. Data for gas detection measurements were corrected to a linear fit of the baseline current.

Procedure for Determining Cu Valency in $Cu_3(HITP)_2$.

The XPS data for $Cu_3(HITP)_2$ suggested the presence of more than one type of Cu site. Since, the formation of Cu metal has been reported during the reaction of Cu(II) salts with o-phenylenediamine (opd), a series of control experiments to probe whether Cu metal was also being formed in the synthesis of $Cu_3(HITP)_2$ was performed. Overall the data, summarized below, indicated that Cu metal was not formed during the synthesis of $Cu_3(HITP)_2$, and therefore the XPS data was interpreted to suggest an inherent mixed-valency of the material.

To determine valency, first, $Cu(OAc)_2$ and opd were reacted under anaerobic conditions to form $Cu(opd)_2$ and Cu metal:

Scheme 1: Reaction of $Cu(OAc)_2$ and opd to form $Cu(opd)_2$

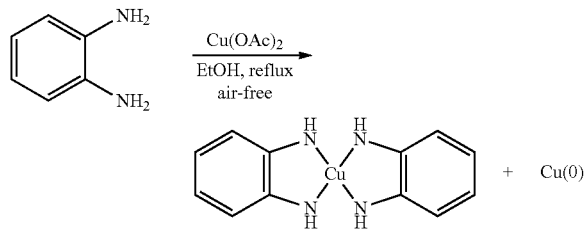

The above reaction proceeded as reported, and Cu metal was clearly observed when PXRD of the crude product was obtained. Furthermore, the Cu 2p region XPS spectrum was dominated by the peaks corresponding to Cu metal. The lack of observed peaks for Cu metal in the PXRD pattern for $Cu_3(HITP)_2$, along with the clear presence of a Cu(II) peak in the XPS spectrum, therefore indicated that Cu metal was not being formed by reduction of Cu(II) in the synthesis of $Cu_3(HITP)_2$.

Additionally, $Cu_3(HITP)_2$ was synthesized via an alternate procedure starting from a Cu(I) precursor:

Scheme 2: Formation of $Cu_3(HITP)_2$ from a Cu(I) precursor.

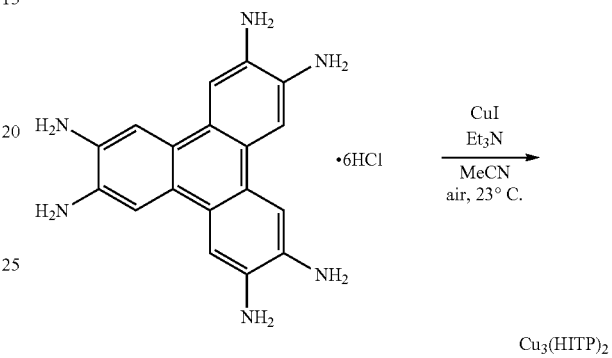

The use of a Cu(I) salt prevented the possibility of Cu(II) serving as an oxidant for the resulting Cu(diamine) complex, and instead both the diamine ligand and the Cu centers underwent aerobic oxidation. PXRD for the product synthesized by this method showed that no Cu metal. XPS for this sample showed the same set of peaks in the Cu 2p region as when starting from Cu(II). Taken together, the above data demonstrates that no Cu metal was formed in the synthesis of $Cu_3(HITP)_2$, and that the material is likely mixed-valent as evidenced by the presence of multiple types of Cu centers.

Working Example 5

This examples the describes the use of a conductive metal-organic framework (MOF) $Ni_3(HITP)_2$ as the sole active material in a supercapacitor. The supercapacitors had a relatively high gravimetric capacitance (i.e., 140 F $g^{-1}$) and volumetric capacitance (i.e., 182 F $cm^{-3}$).

Electrochemical capacitors (EC), also known as supercapacitors or ultracapacitors, are attractive small-to-medium scale capacitors that typically provide relatively high power densities and cyclability (e.g., up to $10^6$ cycles). Electrochemical capacitors are classified into two main types, the electric double-layer capacitors (EDLCs) and pseudocapacitors. EDLCs store energy by forming a layer of electrolyte ions on the surface of a conductive electrode, there is no charge is passed between electrolyte and electrode. While pseudocapacitors store electrical energy faradaically by fast redox reactions near the surface of the electrode, which is usually made from metal oxides or conductive polymers.

Metal-organic frameworks (MOFs) are highly porous extended crystalline materials that can be rationally synthesized by linking organic and inorganic units and accordingly allow for precise control over molecular and crystalline structure. However, conventional MOFs lack intrinsic electrical conductivity, which limits the use of conventional MOFs as an active material for electrochemical capacitors.

In this example, the highly conductive MOF $Ni_3(2,3,6,7,10,11$-hexaiminotriphenylene$)_2$ ($Ni_3(HITP)_2$) described in Working Example 1 was used in a supercapacitor as the sole active material.

As described in Example 1, $Ni_3(HITP)_2$ was synthesized by reaction of 2,3,6,7,10,11-hexaaminotriphenylene hexahydrochloride (HATP*6HCl) with $NiCl_2$ in water with addition of aqueous $NH_3$ under air bubbling. The structure of $Ni_3(HITP)_2$ satisfies the requirements for a supercapacitor. The conductive backbone of $Ni_3(HITP)_2$ is formed by stacked 2D π-conjugated planar layers with sufficiently large open cylindrical channels with a diameter of about 1.5 nm (calculated based on van der Waals accessible surface). The electrical conductivity of $Ni_3(HITP)_2$ powder was ~10 S $cm^{-1}$, which is much higher than conductivity of activated carbon (<1 S $cm^{-1}$), and similar to the conductivity of holey-graphene. The high conductivity of the $Ni_3(HITP)_2$ framework allowed for electrical polarization of the surface and an efficient electrical current flow. The open cylindrical channels facilitated ion transport. $Ni_3(HITP)_2$ material exhibited a large Brunauer-Emmett-Teller (BET) SSA of 514 $m^2$ $gr^{-1}$, as calculated form a nitrogen adsorption isotherm. Pore distribution calculation based on nonlinear density functional theory (NLDFT) fitting of a nitrogen adsorption isotherm assuming cylindrical pores, showed a narrow distribution in the range of 0.8-15 nm, which was consistent with the structure of $Ni_3(HITP)_2$ and calculated shallow potential energy surface for lateral layer displacement. These pores were big enough to accommodate at least 1-2 electrolyte ions (van der Waals ionic radius, $BF_4^-$: 0.5 nm, $NEt_4^+$: 0.7 nm, $EMIM^+$: 0.75 nm). The efficient crystal packing the $Ni_3(HITP)_2$ pressed pallets having densities about 1.3 gr $cm^{-3}$ would lead to a higher volumetric energy densities, and accordingly less dead electrolyte in packed cells, compared to conventional carbon based devices.

The performance of $Ni_3(HITP)_2$ in a supercapacitor was studied using a two-electrode symmetrical cell setup. $Ni_3(HITP)_2$ was pressed into pellets having a thickness of about 100 um thickness and an areal mass loadings of more than about 10 mg $cm^{-2}$. In order to extrapolated the supercapacitive performance of $Ni_3(HITP)_2$ to cell sizes used in commercial applications the areal mass loading should be on the order of 10 mg $cm^{-2}$ for an active material. A typical electrolyte used in supercapacitors, 1.5M tetraethylammonium tetrafluoroborate ($TEABF_4$) in acetonitrile (ACN), was used.

Figure 12:
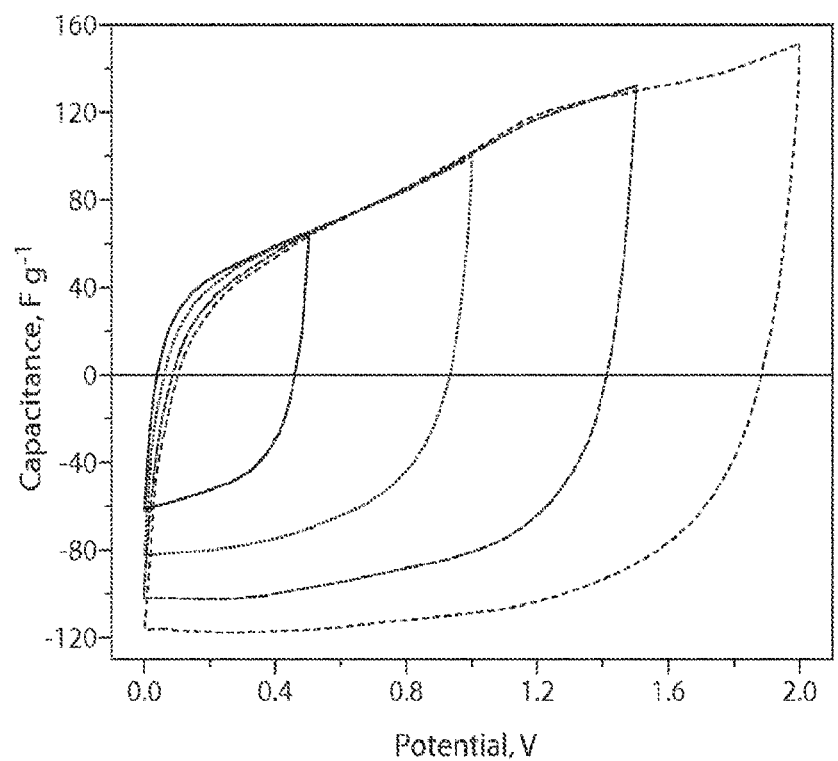
FIG. 12 shows a cyclic voltammogram for a MOF device, according to some embodiments.

Cyclic voltammetry (CV) measurements were performed in various potential ranges and rates. FIG. 12 shows CV at 50 mV/s rate in increasing potential ranges up to 2V. For small potential range up to 0.5V, the cyclic voltammogram showed symmetrical nearly rectangular curve indicating pure electrical-double-layer capacitive behavior. Upon increase of the potential window, the voltammogram showed increased capacitance. This behavior could be explained by the change in ion dynamics as function of potential. The increased capacitance could a result of desolvation of ions, ion-ion interaction, and penetration of ions into the pores.

Next, equivalent series resistance (ESR) was measured. Equivalent series resistance (ESR) describes the combined resistance of the electrolyte, the membrane separator, the internal resistance of the electrode material and current collector, and resistance of the interface between active material and current collector. ESR limits the maximum achievable peak power of a supercapacitor, which is defined as $Pmax=V^2/4*ESR$, where V is nominal cell voltage. ESR may be determined from the potential drop at the beginning of constant current discharge. In such cases, $ESR=\Delta V/2I$, where $\Delta V$ is potential drop and I is discharge current. The assembled $Ni_3(HITP)_2$ EC cell showed a low ESR value of 1.5Ω, which was better than current holey-graphene capacitor at the same areal mass loading.

Figure 13:
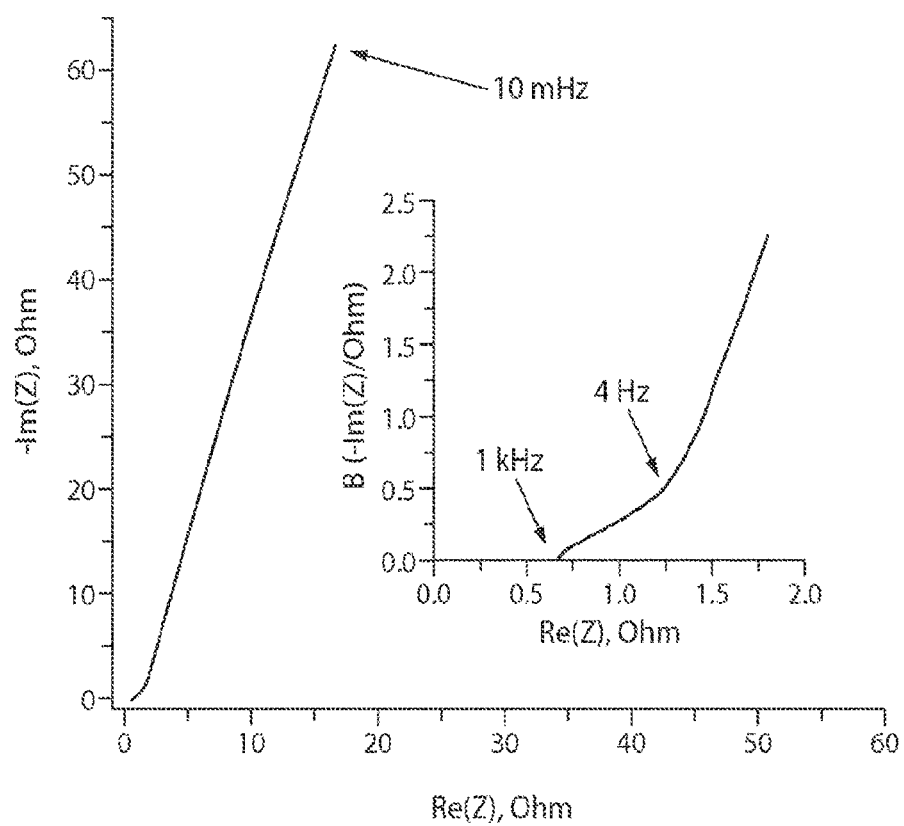
FIG. 13 shows a Nyquist plot for a MOF device, according to some embodiments.

Electrochemical impedance spectroscopy (EIS) in the frequency range of 1 kHz to 10 mHz was also used to investigate the characteristics of the $Ni_3(HITP)_2$. The Nyquist plots, shown in FIG. 13, obtained from EIS were typical for supercapacitors and showed a vertical linear curve in the low frequency range indicating capacitive behavior. FIG. 13 is a Nyquist plot, showing the imaginary part versus the real part of impedance in the 1000 Hz-10 mHz range. The inset shows the high frequency range (1000 Hz 0.5 Hz). The typical transition to Warburg region in intermediate frequencies, which represents the frequency dependent diffusion of ions into the porous electrode, was observed around of 4 Hz. Notably, the capacitive behavior at high frequency attributed to charge transfer resistance was absent.

Figure 14:
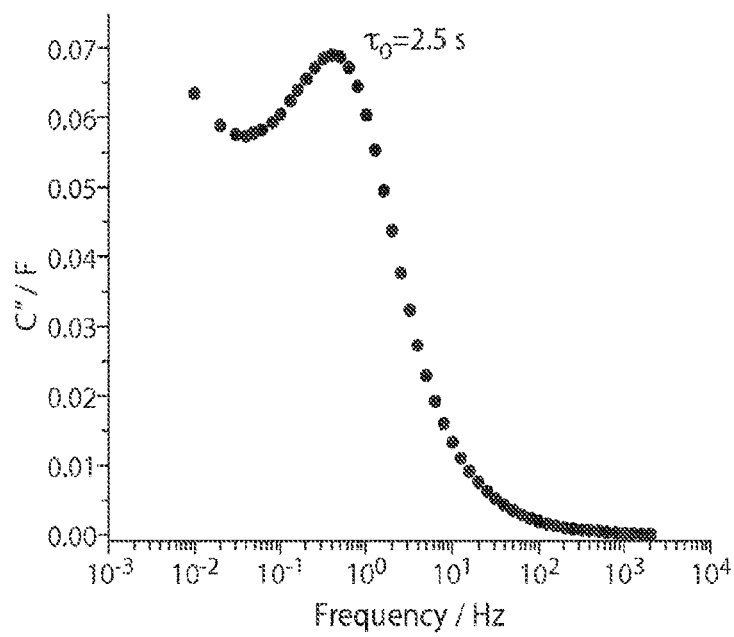
FIG. 14 shows a graph of imaginary capacitance against frequency, according to some embodiments.

Imaginary capacitance C", which corresponds to energy dielectric losses due to an irreversible process, was determined to gain additional insight to the characteristics of the cell. FIG. 14 shows the dependence of the C" on frequency. The frequency $f_0$ of local maximum of the curve is a characteristic of the entire system and can be roughly described as the point where the circuit goes from purely resistive to purely capacitive. The reciprocal of the $f_0$ yields a time constant, $\tau_0$, that is a quantitative measure of how fast the device can be charged and discharged reversibly. The obtained time constant was 2.5 seconds, which was lower than for previously reported activated carbon supercapacitors, which had a time constant of 10 seconds.

Figure 15:
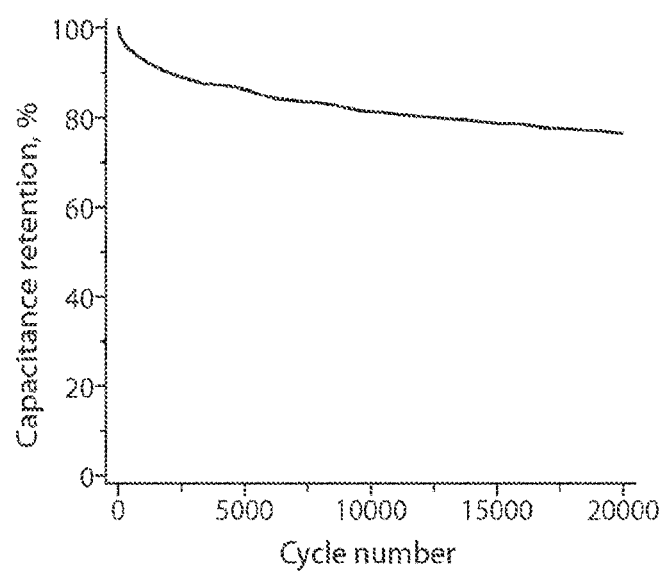
FIG. 15 shows a graph of capacitance retention percentage versus cycle number, according to some embodiments.

The cyclic stability of $Ni_3(HITP)_2$ supercapacitors was also investigated. Cyclic stabilities are important for practical application of supercapacitors. $Ni_3(HITP)_2$ exhibited 76% capacitance retention over 20,000 cycles at high current densities (2 A $g^{-1}$) as shown in FIG. 15. FIG. 15 is a graph of capacitance retention percent versus cycle number.

Specific gravimetric capacitance of $Ni_3(HITP)_2$ at low discharge rate of 0.05 A $g^{-1}$ was 140 F $g^{-1}$, which dropped to 98 F $g^{-1}$ at 1 A $g^{-1}$ and to 34 F $g^{-1}$ at 10 A $g^{-1}$. The obtained capacitances were in the same range as certain porous $sp^2$ carbon materials.

Conductive 2D MOF $Ni_3(HITP)_2$ were used as the sole active material in supercapacitors. $Ni_3(HITP)_2$ showed typical supercapacitive electrical response, low ESR values, and good specific capacitances, which was in the same range as for other porous $sp^2$ carbon materials.

Working Example 6

The following example provides additional details regarding the materials and methods in Working Example 5.

Materials.

Starting materials were purchased from Sigma-Aldrich or TCI and used without further purification. Tris(Dibenzylideneacetone)dipalladium(0), $Pd_2(dba)_3$, was purchased from Oakwood Products, Inc. (Fluorochem Ltd.). Hexane, diethyl ether, ethyl acetate, toluene, acetonitrile and silica-gel were purchased from VWR. THF, toluene and acetonitrile was collected from an alumina column solvent purification system. Tetraethylammonium tetrafluoroborate ($TEABF_4$) have been recrystallized three times from MeOH, and dried under vacuum at 90° C. for 24 h. $Ni_3(HITP)_2$ was prepared according to Example 1.

Methods.

The electrical conductivity of $Ni_3(HITP)_2$ was measured on 7 mm diameter pressed pellet by 4-point van der Pauw method. Keithley 2450 was used as a current source and Keithley 2182A as a voltmeter.

Cell Assembly.

A two electrode symmetrical cell setup, using 13 mm diameter pressed pallets containing 15 mg of $Ni_3(HITP)_2$ was used. Au (200 nm) deposited Al-foil was used as the current collectors. Celgard 3501 was used as a separator. The cell was dried at 100° C. under vacuum (10 mtorr) overnight before electrochemical measurements in the $N_2$ filled glow box.

Electrochemical Characterization and Analysis.

All the electrochemical experiments were carried out using Biologic potentiostat. EIS measurments were performed at open circuit potential with 10 mV amplitude multi-sinusoidal signal with drift correction as implemented in Biologic potentiostat.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A porous metal organic framework (MOF) comprising: a plurality of metal ions, each coordinated with at least one ligand, wherein the at least one ligand comprises at least two sets of ortho-diimine groups arranged about an organic core and has the structure:

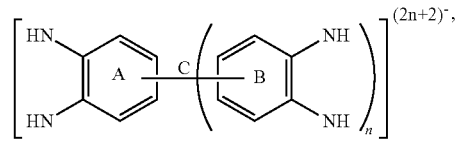

wherein n is 1, 2, or 3, and C represents one or more bonds formed between ring A and each ring B.

2. The MOF of claim 1, wherein a portion of the metal ions are associated with two, three, or four ligands, and each of those ligands is individually associated with one, two, three, or four metal ions.

3. The MOF of claim 1, wherein a portion of the metal ions are associated with two ligands, and each of those ligands is individually associated with two metal ions.

4. The MOF of claim 1, wherein a portion of the metal ions are associated with two ligands, and each of those ligands is individually associated with three metal ions.

5. The MOF of claim 1, wherein n is 1.

6. The MOF of claim 1, wherein n is 2.

7. The MOF of claim 1, wherein n is 3.

8. The MOF of claim 1, wherein the organic core comprises a plurality of fused aryl and/or heteroaryl rings.

9. The MOF of claim 1, wherein the organic core comprises a plurality of fused aryl rings.

10. The MOF of claim 1, wherein the organic core comprises one or more of benzyl, thiophenyl, carbazolyl, pyrrolyl, indolyl, and furanyl rings.

11. A porous metal organic framework (MOF) comprising:
a plurality of metal ions, each coordinated with at least one ligand, wherein the at least one ligand comprises at least two ortho-diimine groups arranged about an organic core and has the structure:

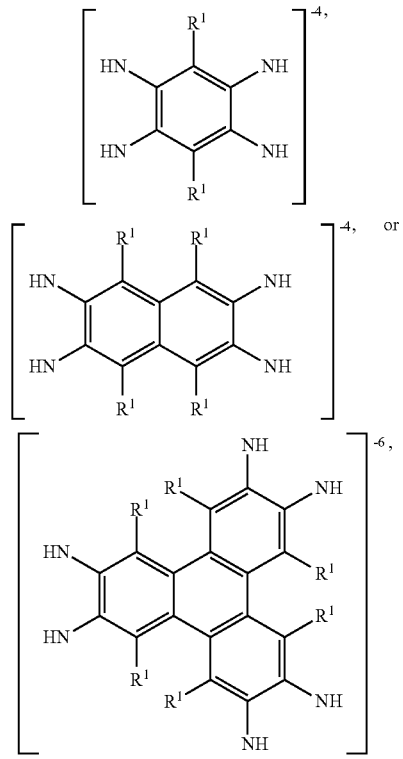

wherein:
each $R^1$ is the same or different and is selected from the group consisting of hydrogen, $-NO_2$, $-R'$, $-F$, $-Cl$, $-Br$, $-I$, $-CN$, $-NC$, $-SO_3R'$, $-SO_3H$, $-OR'$, $-OH$, $-SR'$, $-SH$, $-PO_3R'$, $-PO_3H$, $-CF_3$, $-NR'_2$, $-NHR'$, and $-NH_2$; and
each $R'$ is the same or different and is optionally substituted alkyl or optionally substituted aryl.

12. A porous metal organic framework (MOF) comprising:
a plurality of metal ions, each coordinated with at least one ligand, wherein the at least one ligand comprises at least two ortho-diimine groups arranged about an organic core and has the structure:

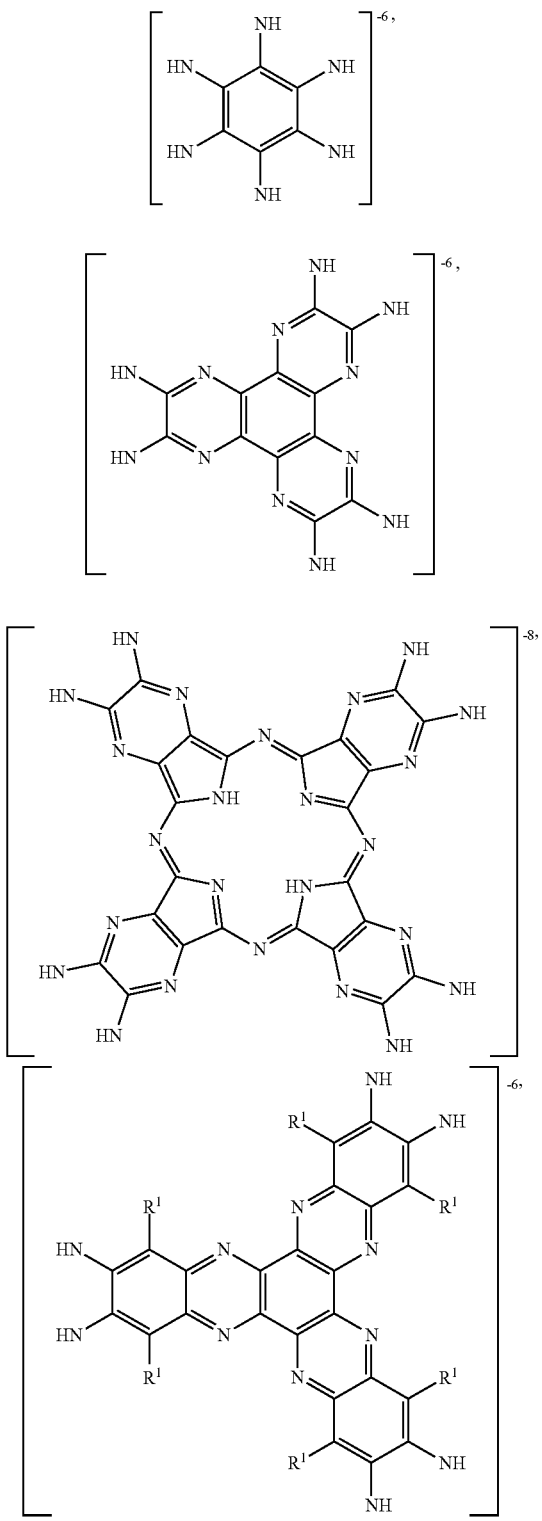

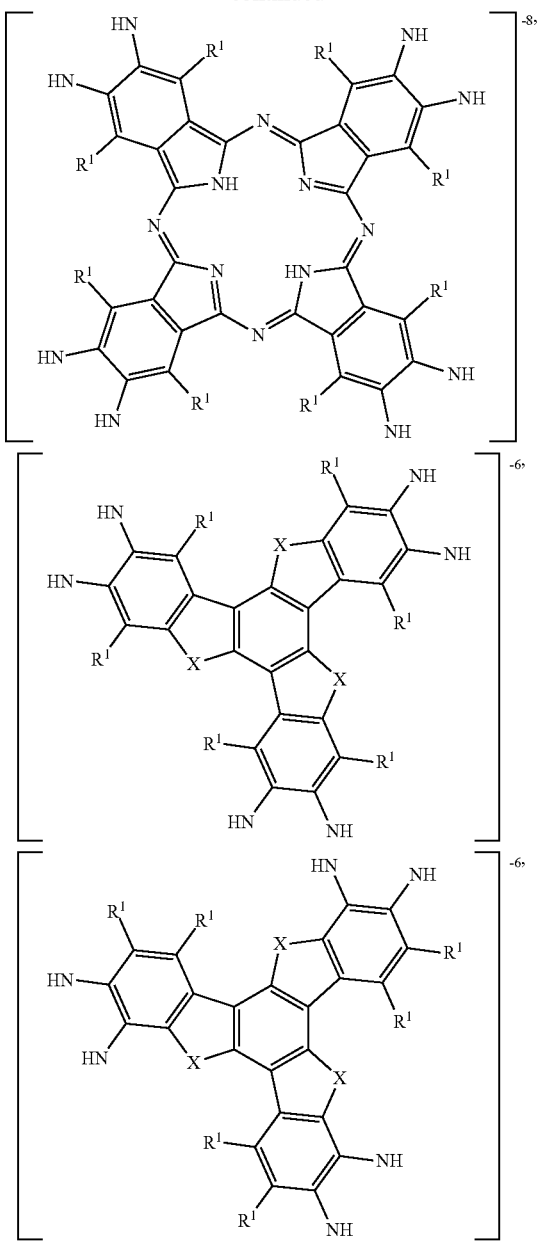

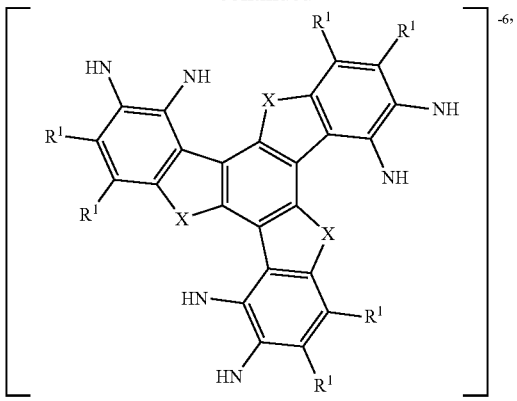

wherein each $R^1$ is the same or different and is selected from the group consisting of hydrogen, $-NO_2$, $-R'$, $-F$, $-Cl$, $-Br$, $-I$, $-CN$, $-NC$, $-SO_3R'$, $-SO_3H$, $-OR'$, $-OH$, $-SR'$, $-SH$, $-PO_3R'$, $-PO_3H$, $-CF_3$, $-NR'_2$, $-NHR'$, and $-NH_2$;

each X is the same or different and is selected from the group consisting of NR', O, S, Se, and Te; and each R' is the same or different and is hydrogen, optionally substituted alkyl, or optionally substituted aryl.

13. A film comprising a MOF as in claim 1.
14. A chemical sensor comprising a MOF of claim 1.
15. An electrochemical capacitor comprising a MOF of claim 1.
16. The MOF of claim 1, wherein each metal ion is $Ni^{2+}$ or $Cu^{2+}$.
17. The MOF of claim 11, wherein each metal ion is $Ni^{2+}$ or $Cu^{2+}$.
18. The MOF of claim 12, wherein each metal ion is $Ni^{2+}$ or $Cu^{2+}$.
19. The MOF of claim 11, wherein each $R^1$ is hydrogen.
20. The MOF of claim 12, wherein each $R^1$ is hydrogen.
21. The MOF of claim 12, wherein each X is NR'.
22. The MOF of claim 21, wherein each R' is hydrogen.
23. The MOF of claim 12, wherein each X is O.
24. The MOF of claim 12, wherein each X is S.
25. A film, a chemical sensor, or an electrochemical capacitor comprising an MOF as in claim 11.
26. A film, a chemical sensor, or an electrochemical capacitor comprising an MOF as in claim 12.

* * * * *